US009655937B2

(12) United States Patent
Jones

(10) Patent No.: US 9,655,937 B2
(45) Date of Patent: May 23, 2017

(54) EXTRACTION DEVICES, SYSTEMS, AND METHODS

(71) Applicant: Connoisseur Holdings, LLC, Portland, OR (US)

(72) Inventor: Andrew Jones, Tigard, OR (US)

(73) Assignee: Connoisseur Holdings, LLC, Portland, OR (US)

( * ) Notice: Subject to any disclaimer, the term of this patent is extended or adjusted under 35 U.S.C. 154(b) by 0 days.

(21) Appl. No.: 15/090,426

(22) Filed: Apr. 4, 2016

(65) Prior Publication Data

US 2016/0213722 A1    Jul. 28, 2016

Related U.S. Application Data

(62) Division of application No. 14/794,665, filed on Jul. 8, 2015, now Pat. No. 9,327,210.

(60) Provisional application No. 62/080,889, filed on Nov. 17, 2014.

(51) Int. Cl.
*B01D 11/02* (2006.01)
*C11B 1/10* (2006.01)
*A61K 36/185* (2006.01)

(52) U.S. Cl.
CPC ........ *A61K 36/185* (2013.01); *B01D 11/0207* (2013.01); *B01D 11/0215* (2013.01); *B01D 11/0219* (2013.01); *B01D 11/0288* (2013.01); *B01D 11/0292* (2013.01); *B01D 11/0296* (2013.01); *C11B 1/10* (2013.01); *A61K 2236/00* (2013.01)

(58) Field of Classification Search
CPC . C11B 1/10; C11B 1/108; C11B 9/025; C11B 9/02; B01D 11/02; B01D 11/0215; B01D 11/028; B01D 11/0288; B01D 11/0253; B01D 11/0219; B01D 11/0292; B01D 11/0296

See application file for complete search history.

(56) References Cited

U.S. PATENT DOCUMENTS

| 1,478,180 | A |   | 12/1923 | Given |
|---|---|---|---|---|
| 1,679,728 | A | * | 8/1928 | Lynn ........................ C11B 1/10 202/169 |
| 2,198,412 | A |   | 4/1940 | McDonald |
| 2,414,418 | A |   | 1/1947 | Lofton, Jr. |
| 3,936,489 | A |   | 2/1976 | Rozsa et al. |
| 5,372,680 | A |   | 12/1994 | Bezdolny et al. |
| 5,516,923 | A |   | 5/1996 | Hebert et al. |

(Continued)

FOREIGN PATENT DOCUMENTS

WO    2015199698    12/2015

OTHER PUBLICATIONS http://www.subzeroscientific.com/#!products/c10g1, retrieved from the Internet on Apr. 28, 2015.

(Continued)

*Primary Examiner* — Katherine Zalasky
(74) *Attorney, Agent, or Firm* — Lane Powell PC

(57) ABSTRACT

Extraction devices, methods, and systems are disclosed. Example devices have a solvent chamber, a plant material chamber, a collection chamber, and a solvent return that create a sealed, closed-cycle extraction and/or solvent purification process. Any extractable plant material can be used in the disclosed devices, methods, and systems although in some examples some form of the *cannabis* plant is used.

29 Claims, 6 Drawing Sheets

(56) References Cited

U.S. PATENT DOCUMENTS

| | | |
|---|---|---|
| 5,525,746 A | 6/1996 | Franke |
| 2004/0147769 A1 | 7/2004 | Davis |
| 2008/0128261 A1 | 6/2008 | Balass |
| 2011/0100894 A1 | 5/2011 | Miller |
| 2011/0133120 A1 | 6/2011 | McGhee |
| 2015/0375136 A1 | 12/2015 | Swan |

OTHER PUBLICATIONS

Tamisium Extractors Inc., "A superior way to extract botanicals," webpage available at <http://tamisiumextractors.com> in Apr. 2012 and Jun. 2012, date obtained through <http://www.archive.org>, 6 pages.
Apollo Valves, "Check Valves Catalog," Dec. 2012, 20 pages.

\* cited by examiner

EXTRACTION DEVICES, SYSTEMS, AND METHODS

CROSS-REFERENCE TO RELATED APPLICATIONS

This application is a division of U.S. Non-Provisional patent application Ser. No. 14/794,665, filed Jul. 8, 2015, now issued U.S. Pat. No. 9,327,210, which claims the benefit of Provisional Patent Application 62/080,889, filed Nov. 17, 2014, the contents of which are all incorporated herein in their entirety.

BACKGROUND

Man has been extracting valuable compounds from plants throughout human time. These extracts range from medicine to poisons, perfumes to flavorings and many others. In today's modern economy, plant extracts are still highly sought and valuable commodities.

One of the main extraction methods existing today is solvent-based extraction in which the plant material containing the extractable compounds is bathed or washed in a solvent. The solvent uptakes the extractable compounds from the plant material and combines the plant material in a solution with the solvent. The compound solution is then purified to remove the solvent and recover the desired extracted compound(s). Often, the purification process involves heating the solution to "boil off" or volatilize the solvent from the solution, leaving the extracted compound(s) behind. Such extraction methods usually use a solvent having a lower boiling point than that of the products so that the solvent can be boiled off without removing or damaging the extracted compound(s).

Typically, the solvents used in such extraction processes are hydrocarbon-based or an alcohol, both of which have low boiling points, but can be explosive or flammable when volatilized. The explosive and flammable nature of the hydrocarbon-based extract processes has led to many injuries and significant property damage as users try to perform these extraction processes.

Additionally, because the hydrocarbon solvents are easy to boil away, the solvents are oftentimes lost as a vapor to the atmosphere during the extraction and purification processes. The loss of the solvent makes the processes expensive to perform because additional solvent must be added for each new extraction process, which requires a large butane supply.

Some of the main solvent-based plant extract processes include those used to extract essential oils, Napetalactone (the main component of catnip) and various pharmaceutical compounds. Also, the rise of medical marijuana and the legalization of *cannabis* and *cannabis*-based products has made *cannabis* plant extracts a legal and marketable pharmaceutical and recreational commodity. One of the major extracts desired from *cannabis* plants is hash oil. Hash oil is concentrated cannabinoids that are extracted from the *cannabis* plant. The main psychoactive component of marijuana is a cannabinoid called tetrahydrocannabinol, better known as THC. Cannabinoids are a class of compounds that act on the cannabinoid receptors of the brain. The interaction of the cannabinoids with the receptors is what causes a user to experience mood-enhancing effects. Marijuana contains a variety of cannabinoids, THC and cannabidiol (CBD) being the major constituents, among many others.

The process of extracting hash oil from *cannabis* plant material often involves running butane, a hydrocarbon-based solvent, through the plant material or soaking the plant material in butane to wash out the cannabinoids. The cannabinoid-rich solvent solution is then purified, often by heating it, which volatilizes the butane and leaves behind the cannabinoid extract. During the volatilization process, the butane solvent is converted into a gaseous form that is then highly flammable and potentially explosive, which presents a significant danger to personal safety and to any surrounding property.

Currently, to assist with recovery of the solvent from the solvent-extract solution, many cannabinoid extract producers use a pump, often a refrigerant recovery pump, to move the vapors from the extract container to a solvent storage container. The pump compresses the gaseous solvent vapors back into a liquid phase. Often these pumps have a mechanical pumping means, are electrically powered and are generally not food safe. Further, the use of such pumps can be dangerous as the pumps are not designed to handle a flammable hydrocarbon. Solvent vapors can leak from the pump and mix with the surrounding environment where they risk being sparked from either the operation of the pump itself or from other external sources. Additionally, any extract process using the recovered solvent risk being contaminated by pump lubricants or adverse chemical reactions with the pump construction.

Therefore, there exists a need for solvent-based extraction processes that can be performed safely without endangering operators and property. Additionally, there exists a need for a clean solvent conservation process to reduce the cost and increase the efficiency of the extraction process.

SUMMARY

Figure 1A:
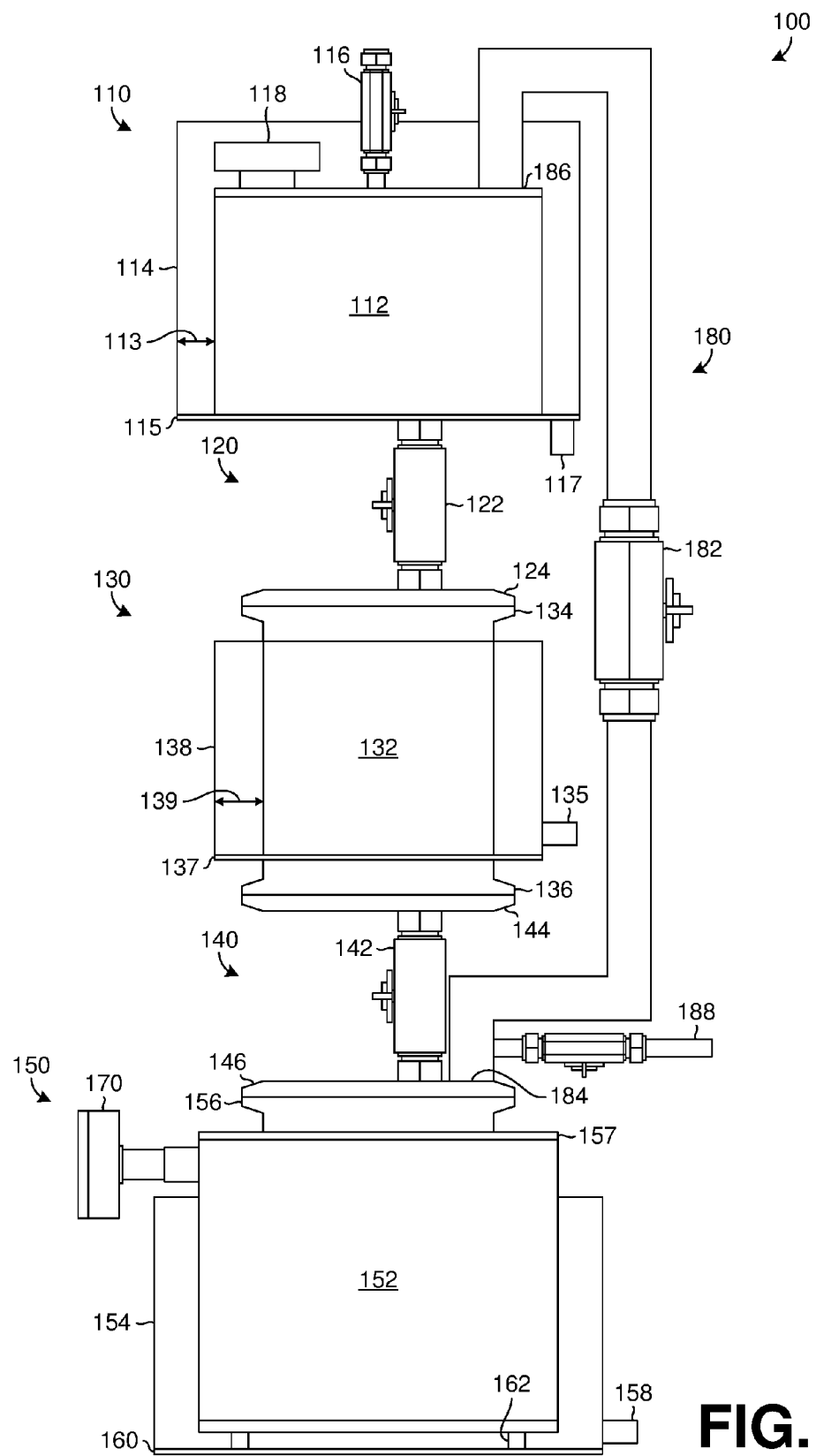
FIG. 1A is an example extraction device in accordance with aspects of the disclosure.

The disclosed extraction device has three chambers, the first is a solvent reservoir; the second is an extraction chamber, which holds the material containing the desired extractable material; and the third is a collection reservoir. Solvent flows from the solvent reservoir into the extraction chamber where the solvent is exposed to and washes through the material, dissolving and carrying away the extractables from the plant material. The solvent-extractables mixture is then collected in the collection reservoir.

The extraction process conducted in the extraction device can be powered by a thermal gradient/heat engine using the phase changing properties of the solvent. In the device disclosed herein, the solvent is maintained in a low-energy, liquid state in the solvent-reservoir. The solvent flows from the solvent reservoir through the extraction chamber that houses the plant material. The contact of the solvent with the plant material extracts compounds/products from the plant material. The solvent-extract solution flows into the collection reservoir which is then warmed to a temperature at which the solvent enters a gaseous phase which causes the gaseous solvent to be released from the extracted compounds.

By heating the collection reservoir to a temperature that volatilizes the solvent, the solvent transforms to a gaseous phase and separates from the solvent-extract solution leaving the extract behind. The remaining extract solution may then be further refined if desired. As the collection reservoir is heated, the gaseous solvent is drawn through a solvent return channel into the solvent reservoir, which can be chilled either continuously or at specific times during the extraction process, such as when the gaseous solvent is released into the return. The gaseous solvent is pulled up the return channel due to the thermal gradient that is created between the chilled solvent reservoir and the heated collection tank.

In the gaseous state, the solvent expands, which creates a pressure in the collection tank that forces the gaseous solvent through the solvent return channel. The solvent return channel terminates in the chilled solvent reservoir where the gaseous solvent condenses into a liquid at the chilled temperature. The condensation of the gaseous solvent reduces the volume of the solvent and thus generates a partial negative pressure which further draws gaseous solvent from the collection reservoir. The condensed solvent may then be recirculated through the device, or collected and stored for use in later extraction processes.

To extract oils, plant material is placed in the extraction chamber. Solvent is then allowed to flow from the solvent storage chamber through a valve and into the extraction chamber where the solvent washes over the plant material, extracting oils from the material as it percolates through. The oil-solvent solution flows from the extraction chamber into the collection chamber through a separate valve. In the collection chamber, the solvent is separated from the extracted oils and is then returned to the storage chamber through the solvent return chamber. The process is entirely sealed within the extraction device and is driven by gravity and the thermal gradient created by heating and/or chilling the various chambers.

DETAILED DESCRIPTION

Extraction Devices

The disclosed extraction devices allow users to extract compounds from plant material using a solvent. The process occurs in a sealed, closed-cycle environment, which allows the user to recover the solvent and limits the likelihood of contamination of the final product. Plant material is placed within an extraction chamber, which is then sealed within the device. The solvent is released from the solvent chamber into the extraction chamber where it is left to extract compounds from the plant material. After the extraction process is completed, the solvent, which now carries the extracted compounds in solution, is drained into a collection reservoir. The collection reservoir is heated to volatilize the solvent, which separates the solvent from the extracted compounds.

As the collection reservoir is heated, the solvent reservoir of the solvent chamber can also be chilled, which creates a temperature gradient between the solvent reservoir and the collection reservoir. Due to the temperature gradient between the collection reservoir and the solvent reservoir, solvent vapors are drawn through a solvent return that connects the collection reservoir and the solvent reservoir. The solvent vapors re-condense in the chilled solvent reservoir due to the low temperature. The recovered liquid solvent may then be stored for later extractions or may be reused in a continuous extraction or solvent purification process. The closed nature of this process helps to maintain the purity of the solvent and the extracted compounds.

If a user desires, the solvent may be allowed to run through the plant material continuously. By chilling solvent reservoir and heating the collection reservoir, the solvent may be recirculated through the device in a continuous manner while running through the material and extracting compounds. The compounds concentrate in the collection reservoir since the solvent is constantly volatilized within the heated collection reservoir. Once the user determines the extraction process is completed, the solvent can be collected in the solvent reservoir and stored for later uses, if desired.

FIG. 1A is a side profile view of an example extraction device 100. The device 100 is composed of three vertically stacked chambers: a solvent chamber 110, an extraction chamber 130 and a collection chamber 150. The chambers are linked by connectors 120 and 140, with a solvent return 180 linking the solvent chamber 110 with the collection chamber 150.

The solvent chamber 110 features an enclosed solvent reservoir 112 that is surrounded by an outer wall 114 separated from the solvent reservoir 112 by a gap 113. The outer wall 114 wraps around the shared base 115, upon which the solvent reservoir 112 is also centered and disposed. The shared base 115 may feature a drain 117 through which the user may drain or dispense contents from the gap, as desired.

The gap 113 allows the solvent reservoir 112 to be surrounded by a fluid bath (not shown) contained between the outer wall 114 and the exterior surface of the solvent reservoir 112. The fluid bath allows a user to adjust and/or regulate the temperature of the solvent reservoir 112 and thus the contents stored within. In the embodiment shown in FIG. 1A, a solvent is stored within the solvent reservoir 112 and is maintained or is cooled to a cool, low energy state by a surrounding cooling bath. Although not shown in FIG. 1A, the solvent reservoir 112 can be raised by spacers to allow the cooling bath to contact its bottom surface and expose greater surface area of the solvent reservoir 112 to the cooling bath.

The cooling bath can be contained in the gap 113 of the extraction device 100 shown in FIG. 1A. The cooling bath can be composed of a mixture of dry ice (solid state $CO_2$) pellets and ethyl-alcohol (ethanol). This combination maintains the solvent reservoir at a temperature ranging from approximately −17° C. to −78° C., which is sufficient to maintain the solvent in a liquid phase. In an example, the solvent is butane, which has a boiling point ranging from −1° C. to 1° C. Additionally, maintaining the solvent reservoir at such a low temperature creates a large temperature differential between the solvent reservoir and the collection reservoir that drives the heat engine powering the device by re-condensing the returning gaseous solvent back into a liquid. Other suitable cooling bath mixtures may be used, as long as the bath maintains the solvent reservoir below the solvent boiling point. It is also desirable to maintain the solvent reservoir at as low a temperature as possible as the efficiency of the system is driven, in part, by the magnitude of the temperature gradient that exists between the chilled solvent reservoir, and the heated collection reservoir.

The side walls of the solvent reservoir 112, the outer wall 114 and the base 115 are constructed of food grade stainless steel, but also may be constructed of other suitable medical and/or food grade materials in other examples. Other such suitable materials include those that are non-reactive with the chosen solvent and those having thermal conductivity. The thermal conductivity allows the solvent reservoir 112, and the contents held within, to be thermally adjusted by the surrounding bath, a high thermal conductivity hastening the transfer of thermal energy from the surrounding fluid bath to the solvent reservoir 112 and contents within. Further, each part, the solvent reservoir 112, outer wall 114 and the base 115, may be constructed of the same or different materials.

Any impurities in the solvent affect the properties of the solvent and may reduce its capacity to extract compounds and/or reduce the thermal capacity, thereby decreasing device and process efficiency. Additionally, any impurities in the solvent may be transferred into the extracted compounds where they may reduce the efficacy, change the quality or cause harm to users of the final product and/or require additional or costly post-extraction processes to remove the entrapped impurities. To further aid in the avoidance of potential impurities, medical and/or food grade materials and design techniques are used throughout the device.

A safety vent, not shown in the figures, may be disposed atop the solvent reservoir 112. The safety vent allows built-up, gaseous solvent to be safely removed from the solvent reservoir 112 to reduce the risk of system overpressure incidents. The vent extends from the upper surface of the solvent reservoir 112 to at least the upper plane of the outer tank 114 to ensure that if the solvent reservoir 112 is submerged in a cooling bath, the outlet of the vent remains open and unblocked. The safety vent is a pipe attached to the solvent reservoir 112 and in fluid communication with the tank interior. Positioned within the safety vent is a diaphragm calibrated to a pre-set pressure. If the interior pressure of the solvent reservoir 112 exceeds the pre-set pressure, the diaphragm opens, venting stored solvent vapors and decreasing the internal pressure of the solvent reservoir 112. Once the internal pressure has fallen to a safe level, below the diaphragm pre-set trigger pressure, the diaphragm closes and reseals the solvent reservoir 112. The one-way nature of the safety vent prevents any outside gas from entering the device. Such contamination could decrease the efficiency of the device and/or contaminate the product.

A view port 118 is disposed on the upper surface of the solvent reservoir 112, as shown in FIG. 1A. The view port 118 is constructed of a transparent material set into a metal housing. The view port 118 is releasably mounted to a protrusion from the solvent reservoir 112 by a threaded connection, but may be permanently affixed in other examples. A seal may be disposed between the view port 118 and the solvent reservoir 112 to prevent solvent vapors from leaking out of the solvent reservoir 112 and to prevent contamination of the solvent by the outside environment. The view port 118, if releasably connected, may be removed when access to the interior of the solvent reservoir 112 interior is necessary, such as for cleaning and maintenance purposes. Alternatively, the view port 118 may extend through a side wall of the solvent reservoir 112 and the outer wall 114. Further, the view port 118 may feature a light to illuminate the interior of the solvent reservoir 112, which could include LED lighting, for example. The lighting source may be located on an interior side of view port 118 where it is exposed to the interior of the solvent reservoir 112. Alternatively, the lighting source may be located in a manner that isolates the source from the interior of the device 100 and/or the exterior environment surrounding the device 100.

The interior of the solvent reservoir 112 can feature markings to assist a user in measuring the quantity and/or quality of the interior contents. The markings can be viewable to a user through the view port 118. In other embodiments of the device 100, the interior markings may be absent as desired or required by the user, use and/or design of the device 100. Also, a temperature gauge, like a thermometer, and/or a pressure gauge can also be included to measure the respective temperature and/or pressure in the solvent reservoir or any other chamber or reservoir described herein.

A solvent inlet 116 extends from the surface of the solvent reservoir 112 and is the entry point for contents, such as a solvent, to be introduced into the solvent reservoir 112. In the embodiment of FIG. 1A, the solvent inlet 116 is a valve to which an external solvent source can be connected. Opening the solvent inlet 116 allows the solvent to flow from the external source into the solvent reservoir 112. The user can assess and observe the fill progress through the view port 118. Once the desired fill level is achieved, the solvent inlet 116 is closed and the external solvent source disconnected.

Alternatively, the solvent inlet 116 can be a spring-loaded inlet valve, similar to those found in butane lighters and refillable air cylinders. An external solvent source (not shown) containing the solvent or other substance to be introduced into the solvent reservoir 112 is connected to the solvent inlet using an appropriate connector. The solvent then flows through the solvent inlet 116 and collects within the solvent reservoir 112. Once the solvent reservoir is filled to a level desired by a user, the external solvent source is disconnected, at which time the solvent inlet 116 is sealed by the internal spring. Using such a valve minimizes or prevents contaminants from the external environment from entering the device 100 through the solvent inlet 116. Contamination of the device 100 by the external environment can adversely affect the solvent and/or the product.

The solvent return 180 connects to the solvent reservoir 112 via an inlet 186. The connection between the solvent return 180 and the solvent reservoir 112 can be releasable or permanent. In the embodiment shown in FIG. 1A, the connection is a permanent weld affixing the solvent return 180 to the solvent chamber 110.

The other end of the solvent return 180 is welded to the top of a sanitary cap 146. In the example shown in FIG. 1A, the solvent return 180 is a rigid structure running between the solvent chamber 110 and the top of fitting 146, allowing fluid communication between the solvent reservoir 112 and the collection reservoir 152. A rigid solvent return 180 can provide structural support and elevate the solvent chamber 110 when the device 100 is assembled.

The solvent chamber 110 is connected to the extraction chamber 130 via a connector 120. The connector 120 features a valve 122 to regulate the flow of the solvent as it exits the solvent chamber 110. The valve 122 is affixed to a threaded extension extending from the shared base 115. Alternatively, the valve 122 can be connected using a compression fitting or directly welded to the shared base 115. The extension is in fluid communication with the solvent reservoir 112. The valve 122 can be controlled manually by a user or electronically controlled by a user or controller. The valve 122 may be variably controlled so that the rate of solvent flowing through it may be varied by a user or other control means. Additionally, there may be a view port disposed about the connector 120 or valve 122 that allows a user to observe the flow of solvent from the solvent chamber 110.

The connector 120 is further affixed to a sanitary cap 124. The sanitary cap 124 is a flat disk, having a chamfered circumference and has a threaded extension to which the valve 122 of the connector 120 is secured. Alternatively, the valve 122 can be connected using a compression fitting or directly welded to the sanitary cap 124. A seal can be disposed on the side opposite the threaded extension and interfaces with a mating surface of a top sanitary ferrule 134 of the extraction chamber 130. The top sanitary ferrule 134 of the extraction chamber 130 and the sanitary cap 124 of the connector 120 are joined by a sanitary connection such as a single pin-hinged clamp. The sanitary connector affixes and compresses the chamfered perimeters of the sanitary cap 124 and the top sanitary ferrule 134 of the extraction chamber 130 to form a seal. Other suitable releasable connections may be used to join the chambers 110 and 130, such as threaded connections.

The extraction chamber 130 of the device 100 as shown in FIG. 1 includes the top sanitary ferrule 134 discussed above, a plant material chamber 132, a bottom sanitary ferrule 136, an outer wall 138 spaced a distance 139 about the plant material chamber 132, a circular base 137 and a drain 158. The plant material chamber 132 is disposed between the top sanitary ferrule 134 and the bottom sanitary ferrule 136. In the embodiment shown in FIG. 1A, the plant material chamber 132 is constructed of food-grade stainless steel, as are the other components of the extraction chamber 130. The plant material chamber 132 can feature view ports to allow a user to observe the extraction process. As with the solvent chamber, the plant material chamber can also include a thermometer or other temperature gauge and a pressure gauge to measure the temperature and the pressure of the plant material chamber.

Alternatively, the plant material chamber 132 can be constructed of glass. The transparent nature of a glass plant material chamber 132 allows a user to observe the extraction process. The chamber 132 may also be constructed of other suitable transparent material. Such suitable materials include those that do not adversely react with the solvent, extract and/or plant materials.

The top sanitary ferrule 134 and bottom sanitary ferrule 136 of the extraction chamber 130 are constructed of food-grade stainless steel and are disposed atop and below the plant material chamber 132. The top sanitary ferrule 134 is affixed to or can be an integrated part of the plant material chamber 132. The bottom sanitary ferrule 136 is affixed to the base of and is in fluid communication with the plant material chamber 132. Both the top sanitary ferrule 134 and bottom sanitary ferrule 136 can have an open geometry. That is, the inner diameters of the top and bottom sanitary ferrule 134, 136 are substantially the same dimensions as the inner diameter of the plant material chamber 132. This allows the user easier access to the interior of the plant material chamber 132.

In the example embodiment in which the plant material chamber 132 is constructed of glass, the plant material chamber 132 is a glass tube, the top and bottom sanitary ferrules 134, 136 providing the top and base for the chamber 132. The top sanitary ferrule 134 and bottom sanitary ferrule 136 can have an interior lip on which seals can be disposed. The upper and lower circumference of the glass plant material chamber 132 rests on the seals respectively. Alternatively, the top 134 and bottom 136 may feature seals about their interior surface, the seals contacting the outer periphery of the glass plant material chamber 132, preventing the interior of the chamber from external environmental intrusion.

In the glass plant material chamber embodiment, a support structure can extend between the top sanitary ferrule 134 and the bottom sanitary ferrule 136, locking the two pieces together with the glass plant material chamber in between. The support structure can be composed of threaded rods with nuts disposed on either side of the top sanitary ferrule 134 and the bottom sanitary ferrule 136. The user tightens the nuts about the top sanitary ferrule 134 and bottom sanitary ferrule 136 to constrain the glass plant material chamber between them.

The outer wall 138 is separated from the plant material chamber 132 by a gap distance 139 about the periphery of the plant material chamber 132. The circular base 137 is connected to the outer wall 138 and disposed about the perimeter of the plant material chamber 132 to form a tank as defined by the gap 139. The gap 139 can be filled with a temperature regulating bath, such as a cooling bath as described above in regards to the solvent chamber, or by a heating/warming bath and can be selectively heated/cooled to help control the temperature gradient between the solvent chamber and the collection chamber. For example, a user can fill the gap 139 surrounding the plant material with a warming bath after the extraction process within the plant material chamber 132 is complete. By warming the chamber 132, any remaining solvent within the chamber 132 can be volatilized and then recovered and used for future extraction processes.

In the embodiment shown in FIG. 1A, the gap 139 is filled with a pre-warmed fluid or mixture after the extraction process is completed. The temperature of the fluid or mixture can be pre-selected by the user to optimize solvent recovery. Once the solvent has been sufficiently recovered, the surrounding bath can be drained through a drain 135. If a steady high temperature bath is required, the drain 135 can be partially open to drain away cooler fluid as the gap 139 is replenished with hot fluid.

Alternative methods of heating the plant material chamber 132 can be used, such as resistive heating elements, thermoelectric heaters and other heating sources. As with the temperature bath discussed above, the heating sources can be temperature controlled to achieve a desired temperature within the plant material chamber 132, if necessary or desired.

The bottom sanitary ferrule 136 is attached to the connector 140 in a manner similar to the top sanitary ferrule 134 connection to the connector 120. The connector 140 is affixed to a top sanitary cap 144 to which the bottom sanitary ferrule 136 of the extraction chamber 130 is connected by a sanitary connection. The top sanitary cap 144 features a seal disposed about the inner perimeter of the cap 144 and contacts a surface of the bottom sanitary ferrule 136, such that when the sanitary connection, such as a single pin-hinged clamp, is engaged, the chamfered bottom sanitary ferrule 136 and chamfered top sanitary cap 144 compress the seal. In the embodiment shown in FIG. 1A, the seal on the top sanitary cap 144 features a mesh filter disposed across the inner diameter of the top sanitary cap 144. The filter prevents plant material from the plant material chamber 132 from traveling through the connector 140.

The connector 140 has a top sanitary cap 144, discussed previously, a bottom sanitary cap 146 and a valve 142. The valve 142 is attached to a threaded extension of the top sanitary cap 144. Alternatively, the valve 142 can be connected using a compression fitting or directly welded to the top sanitary cap 144. The threaded extension of the top sanitary cap 144 is in fluid communication with the interior of the plant material chamber 132. The valve 142 can be manually controlled by a user or can be electronically controlled by a user or controller. Additionally, there may be a view port disposed about the connector 140 or valve 142 that allows a user to observe the flow of solvent-extract solution from the extraction chamber 130. The bottom sanitary cap 146 is connected to the valve 142 in a similar manner as the top sanitary cap 144. The bottom sanitary cap 146 includes a threaded extension to which the valve 142 is affixed and the threaded extension is in fluid communication with the collection chamber 150. Alternatively, the valve 142 can be connected using a compression fitting or directly welded to the bottom sanitary cap 146.

The collection chamber 150 shown in FIG. 1A features a collection reservoir 152, an outer wall 154, a sanitary ferrule 156, a base 160, spacers 162, a pressure indicator 170 and a solvent return outlet 184. The collection reservoir 152 is a tank of a similar construction as the solvent reservoir 112. The collection reservoir 152 collects the solvent-extract solution from the extraction chamber 130. The collection reservoir 152 is elevated from the base 160 by spacers 162 although in alternative examples the collection reservoir 152 sits directly on the base 160. In the example shown in FIG. 1A, a fluid bath is disposed about the reservoir 152 and is contained by the outer wall 154. The spacers 162 allow the bath to contact more surface area of the collection reservoir 152.

The sanitary ferrule 156 is connected to a top plate 157 of the collection reservoir 152, as shown in the embodiment of FIG. 1A. The sanitary ferrule 156 can be removably connected, such as by a threaded connection or other removable attachment options, to the top plate 157. The top plate 157 can also be removably connected to the collection reservoir 152 or permanently attached by welding or other permanent attachment options. Alternatively, the sanitary ferrule 156 can be integrated with the top plate 157 to form a single piece that is removably attached to the collection reservoir 152. The sanitary ferrule 156 is in fluid communication with the collection reservoir 152 of the collection chamber 150. Further, a view port can be disposed on the sanitary ferrule 156, top plate 157 or in any other location such that a user may observe the contents of the reservoir 152.

A drain outlet 158 is disposed on the outer wall 154 and is in fluid communication with the gap surrounding the collection reservoir 152. The fluid bath surrounding the collection reservoir 152 can be drained through the drain outlet 158 after the extraction process is completed.

A pressure indicator 170 is in fluid communication with the interior of the collection reservoir 152 and allows a user to observe and monitor the interior pressure. The pressure indicator can indicate a positive pressure, a negative pressure or combination thereof. The pressure indicator 170 is disposed on a sidewall of the reservoir 152 but may be disposed elsewhere as required or desired.

The solvent return 180 is connected to the outlet 184 and is disposed on the sanitary ferrule 156 of the collection reservoir 152. The solvent return 180 is in fluid communication with the collection reservoir 152 when the sanitary ferrule 156 is in place and allows gaseous solvent to travel from the collection reservoir 152 to the solvent reservoir 112. The solvent return 180 may be permanently or releasably connected to the sanitary ferrule 156. In the embodiment shown in FIG. 1A, the solvent return 180 is welded to the sanitary ferrule 156.

The solvent return 180 is a food-grade stainless steel conduit that fluidly links the collection chamber 150 with the solvent storage chamber 110. The solvent return 180 provides the path for the gaseous solvent to return to the solvent chamber and re-condense to its liquid form, thus providing a fully-sealed extraction system. The solvent return 180 has a valve 182 to regulate the flow of gaseous solvent from the collection reservoir 152 to the solvent reservoir 112. The valve 182 is in-line with the solvent return 180 and is connected via releasable threaded connections. In the embodiment of FIG. 1A, the solvent return 180 is welded to the solvent storage chamber 110 and the sanitary ferrule 156 of the collection reservoir 152. While the valve is disposed in the solvent return 180, the solvent chamber 110 and the sanitary ferrule 156 of the collection reservoir 152 are effectively a single unit linked by a rigid form of the solvent return 180. By separating the solvent return 180 at the valve 182, the two sections, the solvent chamber 110 and the sanitary ferrule 156 may be disjoined from one another. The rigid solvent return 180 provides structural support for the vertically stacked chambers and a rigid, parallel return path to fully seal the extraction system.

Alternatively, in example devices that are self-supporting or are supported externally, the solvent return 180 can be a flexible or semi-rigid connection. Such connections can include a hose, flexible piping, high pressure flexible line or other suitable connection option.

A purge valve 188 is included on the solvent return 180. The purge valve 188 is disposed on the solvent return 180 such that it is in fluid communication with the interior of the collection reservoir 152, regardless of the position of the valve 182 on the solvent return 180. The purge valve 188 allows the user to purge or decrease the amount of oxygen within the device 100 before starting an extraction process and/or loading the solvent. When using a combustible or flammable solvent, the purging of oxygen from the system assists in lowering the risk of solvent ignition. The valve 188 may be a one- or two-way valve or may be actuated by a user or other control means. The purge of oxygen or other atmosphere within the device may be accomplished by introducing a secondary, inert gas that displaces the existing gas within the device 100 through the valve 188. Alternatively, a vacuum can be created within the device, the evacuated air being drawn through the valve 188 by a mechanical means. By creating a vacuum or low pressure within the device, the amount of oxygen within the device is preferably below the level required for ignition and/or combustion of the solvent.

Additionally, the purge valve 188 can act as a pressure relief valve for the collection reservoir 152. The purge valve 188 is in fluid communication with the interior of the collection reservoir 152, opening the purge valve 188 can vent stored pressure from within the interior of the collection reservoir 152 as necessary.

Figure 1B:
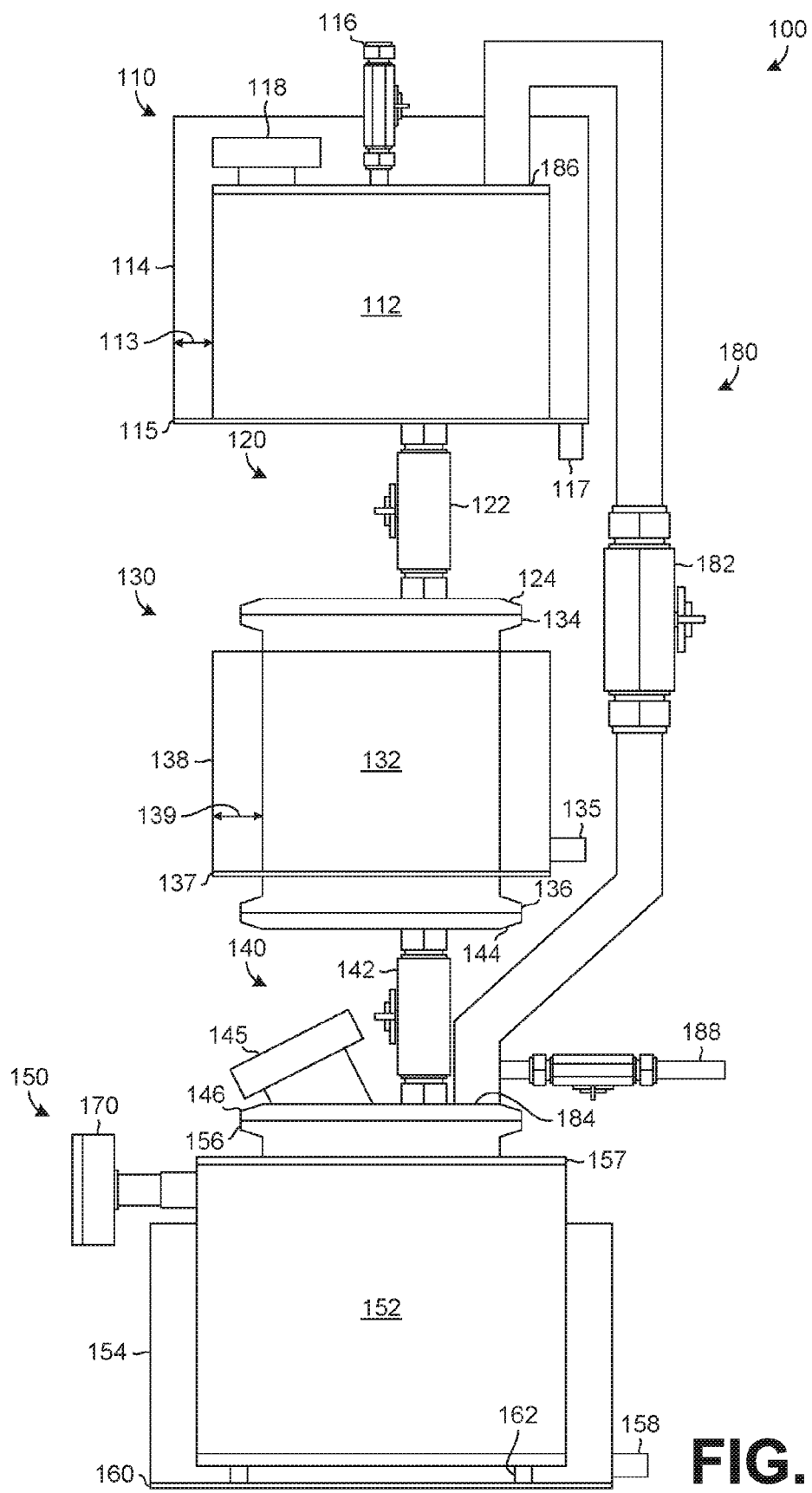
FIG. 1B is a variation of the example extraction device shown in FIG. 1A.

FIG. 1B is an alternative embodiment of the device 100 of FIG. 1A. The device 100, as shown in FIG. 1B, includes a view port 145 disposed on the bottom sanitary cap 146 of the connector 140. The view port 145 allows the user to view the interior of the collection reservoir 152. A light source, such as LEDs, can be disposed about the interior, or exterior, of the view port 145 and light the interior of the collection reservoir 152 for improved user viewing. The collection reservoir 152 can feature internal markings similar to those of the solvent reservoir 112, assisting the user in measuring the filled volume of the collection reservoir 152 through the view port 145.

Figure 2A:
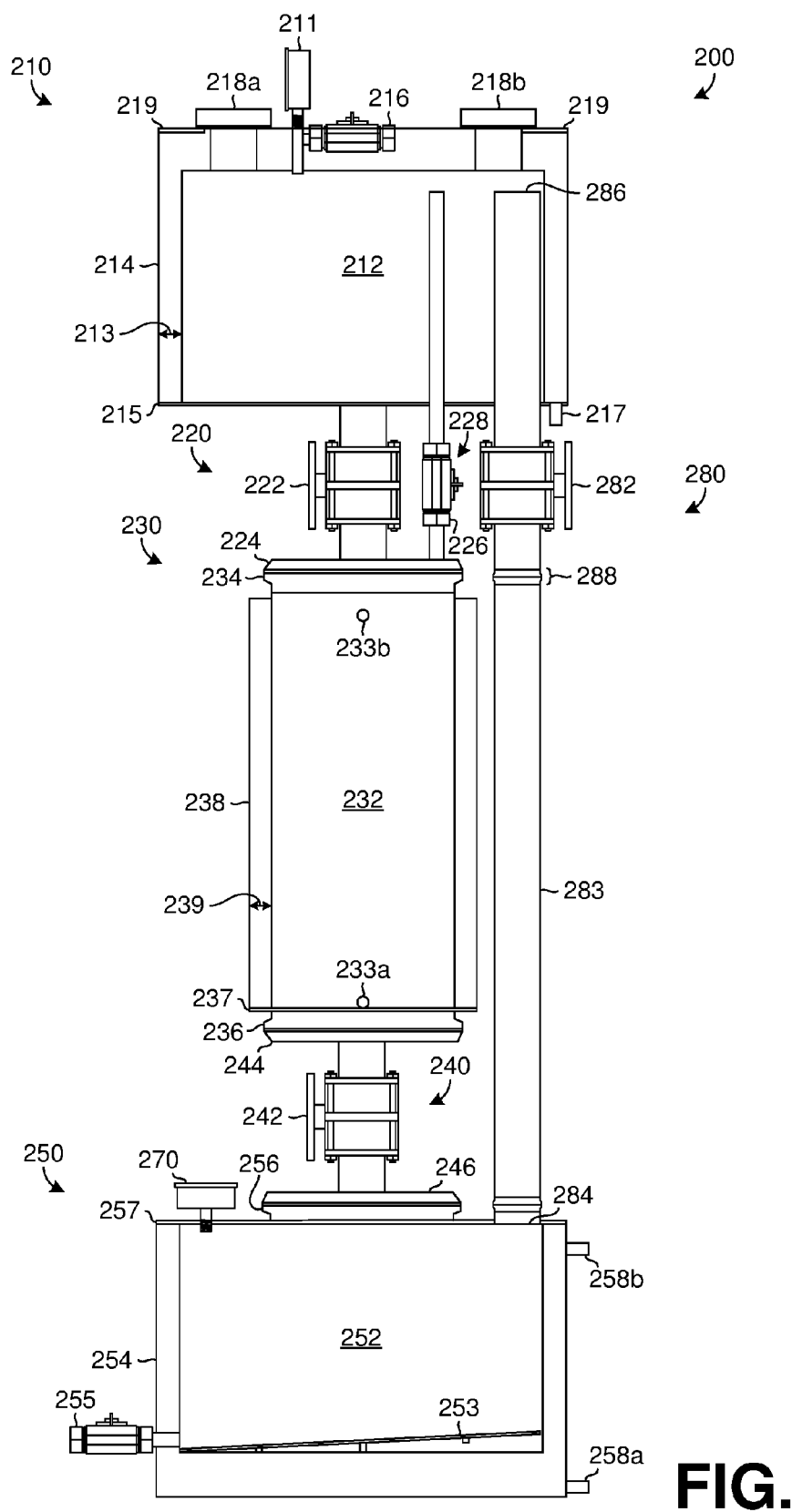
FIG. 2A is another example extraction device according to aspects of the disclosure.

FIG. 2A is another embodiment of the extraction device 200 that is composed of three different sections, a solvent chamber 210, an extraction chamber 230 and a collection chamber 250, which are connected by connectors, 220 and 240, and a return 280. The solvent chamber 210 includes a solvent reservoir 212 surrounded by an outer wall 214 and separated by a gap 213. The outer wall 214 and solvent reservoir 212 are attached to a shared base 215. The shared base 215 includes a drain 217 through which the contents of the gap 213 can be drained.

The solvent reservoir 212 has a removable cap, 218a or 218b that a user can remove for improved access to the interior of the reservoir 212. Alternatively, the solvent reservoir 212 is not required to have a cap and can be completely enclosed, which may be desirable to prevent contamination of the solvent by an external environment.

The gap 213 allows the solvent reservoir 212 to be surrounded by a fluid bath. As discussed with the previous embodiments, the fluid bath is a cold bath that can be composed of many different materials and mixtures. The low temperature of the solvent chamber 210 and the heated collection chamber 230 create a temperature gradient that drives the solvent recovery process.

Additionally, a splashguard 219 is included about the inner periphery of the outer wall 214. The splashguard 219 is affixed to the outer wall 214 and extends over the gap and partially covers the periphery of the solvent reservoir 212. Alternatively, the splashguard 219 can be a removable element that interfaces with the outer wall 214 for support.

The solvent reservoir 212, the outer wall 214 and the base 215 are made of food-grade stainless steel, a non-reactive material that will not contaminate the solvent or finished product. Alternative materials can be used for the construction of the various components to preserve the quality of the extract and solvent.

The solvent reservoir 212 includes a view port, 218a or 218b, through which the user can observe the interior of the reservoir 212. As previously discussed, the view port, 218a or 218b, include a transparent top portion through which the user can observe the interior of the solvent reservoir 212. Additionally, lights, such as LEDs, can be disposed about the interior periphery, or exterior, of the view port 218a or 218b to assist the user with observations.

In the example device 200 shown in FIG. 2A, either of the elements 218a and 218b can be a cap and/or a view port. That is, 218a can be a view port and 218b can be a solid cap, or vice versa. Alternatively, both 218a and 218b can be view ports, with one or both removably connected to the solvent reservoir 212.

A pressure gauge 211 and a solvent inlet 216 are in fluid communication with the interior of the solvent reservoir 212. The pressure gauge 211 allows the user to determine an interior pressure of the reservoir 212. The user can respond to pressure indications as necessary, such as by venting stored pressure within the solvent reservoir 212 to prevent an over-pressurization event which could lead to catastrophic failure of the device. The interior pressure of the solvent reservoir 212 can be vented through the solvent inlet 216 by actuation of the valve. The actuation of the valve can be done by a user or remotely by a manual or automatic actuator. Additionally, the pressure gauge can be configured to automatically actuate the valve at a given pressure to prevent an undue accumulation of pressure or volatilized solvent.

Solvent from the solvent reservoir 212 flows into the extraction chamber 230 through the connector 220. The connector 220 includes a sanitary valve 222 that is disposed between and in fluid communication with the solvent chamber 210 and the extraction chamber 230. The sanitary valve is held between the two chambers using a compression fitting. Alternatively, the sanitary valve 222 can be directly welded to one or both of the solvent chamber 210 and the extraction chamber 230.

The connector 220 further includes a sanitary cap 224 to which the valve 222 is also connected. The sanitary cap 224 and the sanitary ferrule 234 form a sanitary connection between the connector 220 and the extraction chamber 230 when a compression clamp, such as a single pin-hinged clamp is locked about the chamfered circumference of the two pieces 224 and 234.

A solvent return 228 is also included on the sanitary cap 224. The solvent return is in fluid communication with the plant material chamber 232 of the extraction chamber 230 and the solvent reservoir 212. As the remaining solvent within the plant material chamber 232 is volatilized after the extraction process, the solvent vapors travel through the solvent return 228 and recondenses in the chilled solvent reservoir 212. The solvent return 228 enters the solvent reservoir 212 and extends past the level of the solvent within. In doing so, the solvent within the reservoir 212 cannot travel back down the return 228 and into the extraction chamber 230. A valve 226 is disposed on the solvent return 228 to allow the user to regulate the flow of the volatilized solvent from the extraction chamber 230.

The extraction chamber 230 includes a plant material chamber 232, an outer wall 238, a circular base 237, a top sanitary ferrule 234 and a bottom sanitary ferrule 236. As discussed previously, the components of the extraction chamber 230 are constructed from food-grade stainless steel using food-grade manufacturing techniques and processes.

The plant material chamber 232 is topped with a removable or integrated top sanitary ferrule 234 that is a portion of the sanitary connection between the extraction chamber 230 and connector 220. The top sanitary ferrule 234 has an open diameter approximately equal to that of the inner diameter of the plant material chamber 232 to allow the user easier access to the interior of the plant material chamber 232. The extract containing plant material is placed in the plant material chamber 232.

A circular base 237 is disposed about the periphery of the plant material chamber 232 and spaces the outer wall 238 a distance 239 from the said periphery. The circular base 237 provides the base for the tank formed by the outer wall 238 and gap 239. The gap 239 can be filled with a temperature bath, preferably a warm or hot water bath, after the extraction process is completed. The temperature bath heats the plant material chamber 232, which volatilizes the remaining solvent that then flows through the solvent return 228 back into the solvent reservoir 212.

The outer wall 238 includes openings 233a and 233b through which the temperature bath can be added and circulated about the plant material chamber 232. The temperature bath can flow in through the opening 233a, filling the gap 239 from the bottom up. At the top, the temperature bath flows out through the opening 233b, which allows for a steady replenishment of pre-heated temperature bath to be circulated about the plant material chamber 232. The temperature bath exiting the opening 233b is at a lower temperature, as it has transferred thermal energy to the plant material chamber 232, then the pre-heated temperature bath entering the gap 239 through the opening 233a. The temperature bath circulating within the gap 239 can have a pre-selected and/or controllable temperature, which can be controllable by a user or electronic controller, in order to achieve maximal efficiency of solvent recovery.

The bottom sanitary ferrule 236 can be attached or integrated to the base of the plant material chamber 232. The bottom sanitary ferrule 236 interfaces with a sanitary cap 244 of the connector 240 to form a sanitary connection between the extraction chamber 230 and the connector 240.

The base of the plant material chamber 232 and/or the sanitary ferrule 236 can include a filter that prevents plant material from entering the connector 240 but allows the extract-rich solvent solution to pass through. Additionally, the filter can be a filter that removes or limits the amount of undesirable compounds that pass from the extraction chamber 230 into the collection chamber 250.

The connector 240 includes a sanitary valve 242 disposed between a sanitary cap 244 and a bottom sanitary cap 246. The connector 240 facilitates and regulates fluid communication between the extraction chamber 230 and the collection chamber 250.

The collection chamber 250 includes a collection reservoir 252, an outer tank 254 and a shared top 257. A sanitary ferrule 256 is affixed or integrated with the shared top 257. The sanitary ferrule 256 interfaces with the lower sanitary cap 246 of the connector 240 to form a sanitary connection between the extraction chamber and the connector 240.

The collection reservoir 252 is affixed or integrated with the shared top 257. This arrangement allows the suspension of the collection reservoir 252 within the outer tank 254. The outer tank 254 is filled with a temperature bath that surrounds the collection reservoir 252 and assists with the separation of the extract from the solvent and the recovery of the solvent. Preferably, the temperature bath is a warm or hot water bath that transfers sufficient thermal energy into the solvent-extract solution within the collection reservoir 252 to volatilize the solvent. Volatilizing the solvent separates the solvent from the solvent-extract solution and the solvent vapors rise through the solvent return 280 to be recovered in the solvent reservoir 212.

The outer tank 254 includes an inlet 258a through which the temperature bath can be introduced into the outer tank 254. The inlet 258a can also function as a drain to drain the bath contained by the outer tank 254 after a refinement or extraction process is completed.

The outer tank 254 includes an outlet 258b, through which the temperature bath exits the outer tank 254 as additional temperature bath is introduced though the inlet 258a. As newly heated temperature bath is introduced through the inlet 258a, temperature bath can be displaced through the outlet 258b. The outlet 258b can be connected to the inlet 233a of the outer wall 238 of the extraction chamber 230. In this arrangement, the temperature bath is circulated about the collection reservoir 252 before being displace to circulate about the plant material chamber 232.

The collection reservoir 252 includes an inclined floor 253 that can be added to or integrated with the reservoir 252. The inclined floor 253 directs the extract solution to the outlet 255 through which the extract solution can be removed from the collection reservoir 252.

Alternatively, the collection reservoir 252 can be constructed to have a sloping floor itself. Such a design removes the need for an inclined floor 253 within the reservoir 252. The inclined floor 253 or the alternative embodiment of a collection chamber with an integrated slopped floor can have an adjustable incline in some examples that can be adjusted manually or automatically.

A pressure gauge 270 is in fluid communication with the interior of the collection reservoir 252 and indicates the stored pressure to a user. The pressure indicator 270 can indicate a positive pressure, a negative pressure or a combination thereof. As the solvent-extract solution is heated and the solvent is vaporized, the pressure within the solvent reservoir 252 rises if the solvent vapors are constrained. The pressure gauge allows the user to measure the interior pressure of the reservoir 252 so that the user can take appropriate safety action should the internal pressure of the collection chamber approach a critical level. Venting the constrained pressure can prevent catastrophic failure of the device 200.

A solvent return 280 fluidly connects the collection reservoir 252 and the solvent reservoir 212. The return 280 assists the recovery of the solvent after the extraction process is completed. As the solvent within the collection reservoir 252 is heated and volatilized, the volatilized solvent flows up the return 280 and into the chilled solvent reservoir 212 where it recondenses back into liquid solvent. The return 280 includes a sanitary ferrule 284 extending from the collection reservoir 252 a length of conduit 283 and a sanitary valve 282. The length of conduit 283 is connected to the sanitary ferrule 284 by a sanitary connection and extends vertically to the valve 282, which is connected by a sanitary connection 288.

The sanitary valve 282 regulates and controls the flow of volatilized solvent from the collection reservoir 252 to the solvent reservoir 212. The return 280 extends from the sanitary valve 282 and into the solvent reservoir 212 with an outlet 286 located above the level of the solvent. As the vapors flow through the outlet 286 and recondense into liquid solvent, the elevated position of the outlet 286 prevents liquid solvent from flowing back down the return 280.

The vertical nature of the solvent return 280 shrinks the overall footprint of the device 200.

Figure 2B:
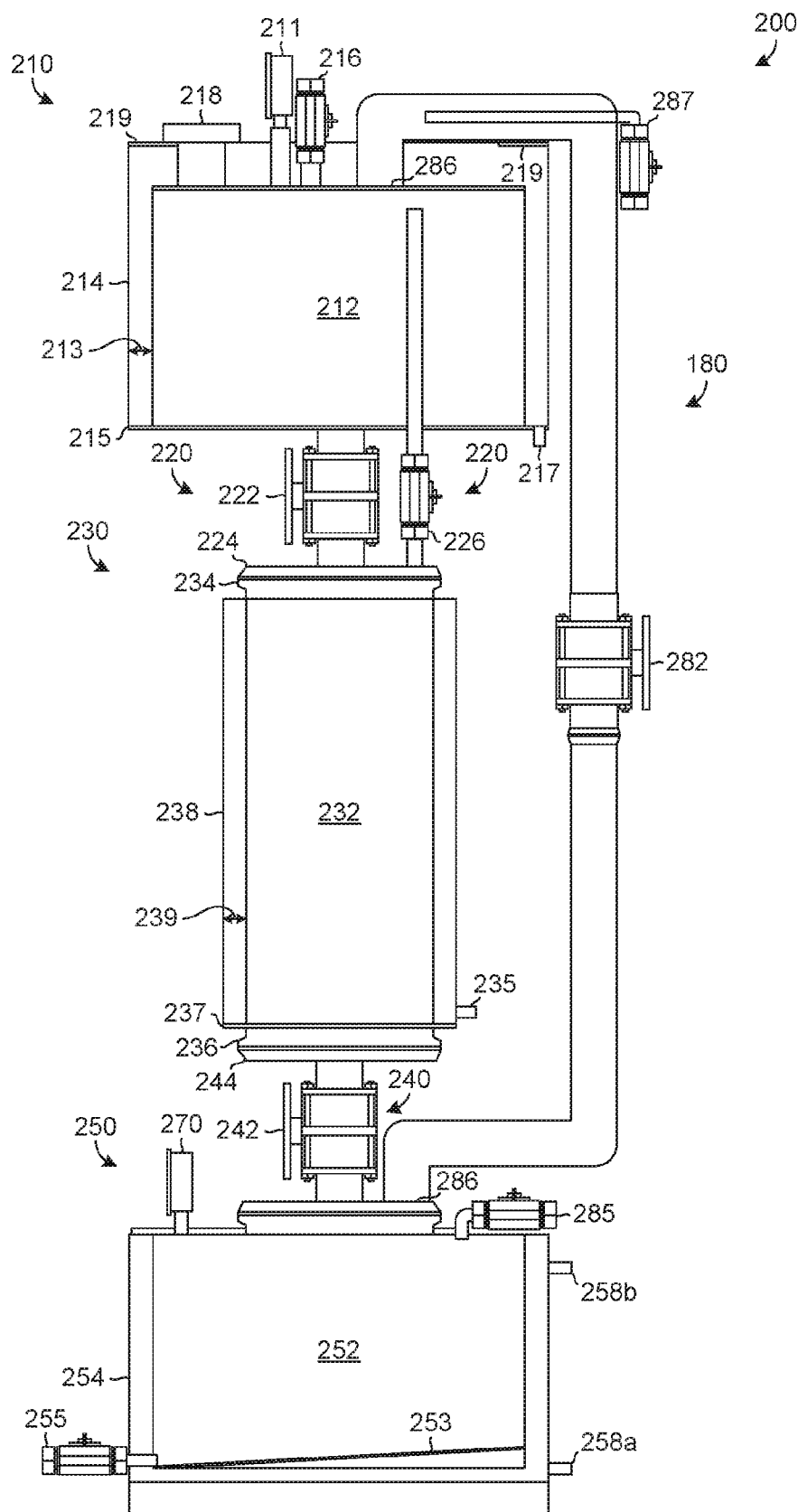
FIG. 2B is a variation of the example extraction device shown in FIG. 2A.

FIG. 2B is an embodiment of an extraction device 200 similar to the device of FIG. 2A with some modifications and additions.

The solvent chamber 210 of the device 200 of FIG. 2B has a single view port 218 through which the user can observe and monitor the interior of the solvent reservoir 212.

The return 280 of the device 200 of FIG. 2B is similar in nature to the solvent return 180 of the device 100 of FIGS. 1A and 1B. The return 280 is in fluid communication with the collection chamber 250 through the sanitary ferrule 284. The return 280 includes a sanitary valve 282 disposed along its length. The sanitary valve 282 regulates and controls the flow of the volatilized solvent from the collection reservoir 252 into the solvent reservoir 212. The return 280 terminates at the top of the solvent reservoir 212 at an outlet 286.

An oxygen purge element 285, like that of 188 of FIGS. 1A and 1B, is connected to and in fluid communication with the collection reservoir 252. The oxygen purge element 285 assists the user in purging the device of oxygen and other unwanted gases prior to an extraction process occurring.

The return 280 also features an outlet and valve 287. The outlet and valve 287 allows access to the device 200 interior from the outside. Evacuation of or creation of a vacuum within the device 200 can be done through the outlet and valve 287. A vacuum pump, a venturi pump or other evacuation device can be connected to the outlet and valve 287 to evacuate or create a vacuum within the device 200.

Figure 3:
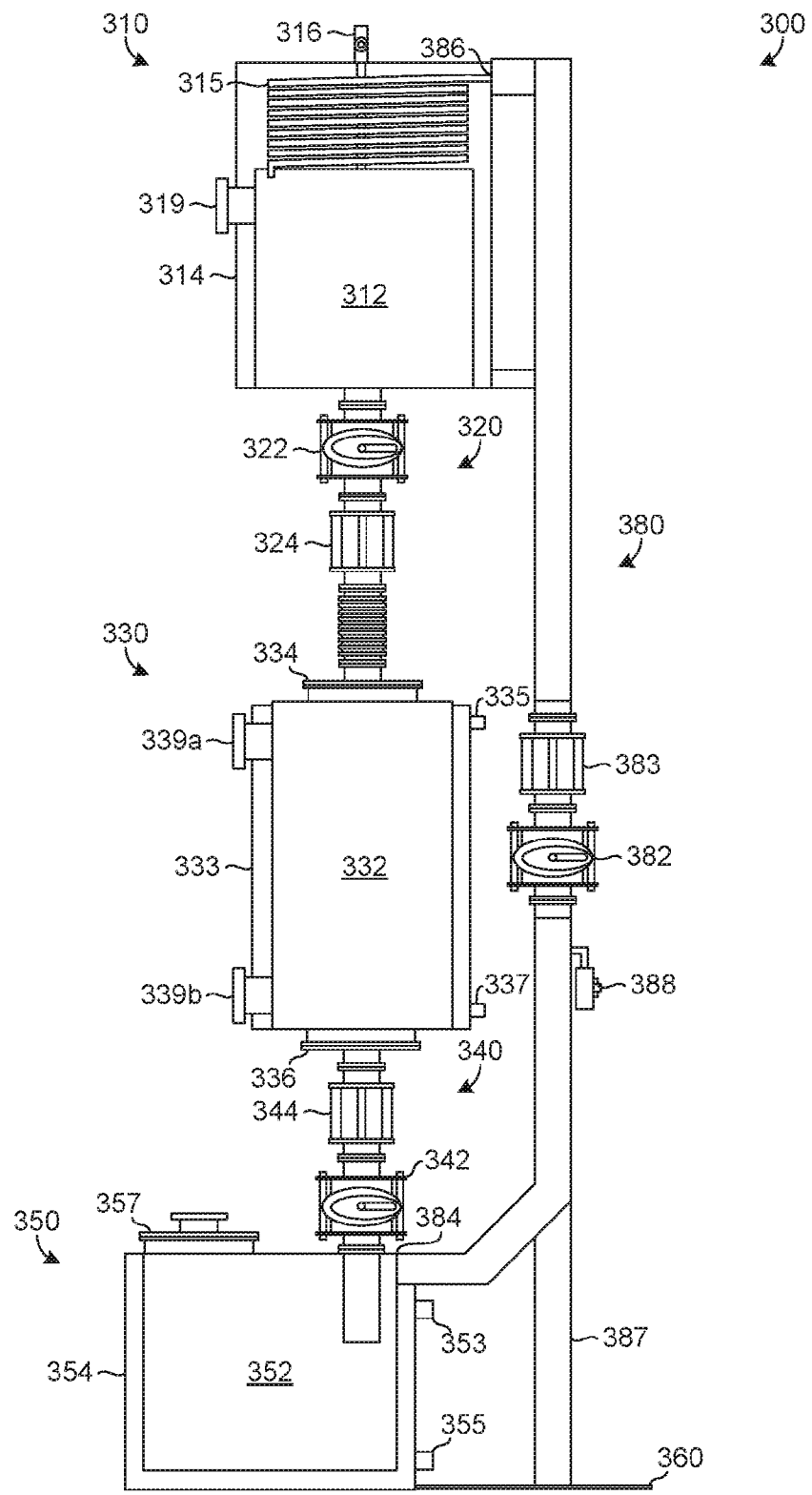
FIG. 3 is still another example extraction device according to aspects of the disclosure.

FIG. 3 shows a second embodiment of the extraction device. The device 300 of FIG. 3 is designed for larger, commercial extraction batches although it can also accommodate smaller batches, as desired. The device 300 generally functions similarly to the devices 100 shown in FIGS. 1A-1B with the addition of a condensing coil 315 to the solvent chamber 310. After an extraction has been performed, the user heats the collection reservoir 352 which volatilizes the solvent, separating it from the extracts. The gaseous solvent travels through the solvent return 380 and into the condensing coil 315. The condensing coil 315 sits in the outer tank 314 to which a cold bath has been added. As the gaseous solvent flows through the cool condensing coil 315 it recondenses into a liquid phase that flows into the solvent reservoir 312. The condensing coil 315 provides increased surface area for the thermal energy transfer from the gaseous solvent to the surrounding cool bath.

The condensing coil 315 of the device of FIG. 3 is disposed in the solvent chamber 310. The condensing coil 315 is connected to and located above the solvent reservoir 312 and connected to the solvent return 380 at the inlet 386. The condensing coil 315 is constructed of material having a high thermal conductivity, such as a metal or other suitable material. It is desirable that the coil is highly thermally conductive to more quickly and efficiently condense the returning gaseous solvent back into a liquid phase.

The outer tank 314 of the solvent chamber 310 extends vertically past the solvent reservoir 312 and around condensing coil 315, which completely submerges the condensing coil 315 in the surrounding cold bath. Gaseous solvent, from the heated collection reservoir 352, enters the condensing coil 315 from the return 380 through the inlet 386. In the condensing coil 315, thermal energy from the gaseous solvent is transferred to the surrounding cool bath. The large surface area of the condensing coil 315, in contact with the cool bath, increases the conductive heat transfer which speeds condensation of the gaseous solvent vapor into liquid solvent. The condensed solvent then flows through the remainder of the condensing coil 315 where it discharges into the solvent reservoir 312.

A solvent inlet 316 is connected to the solvent reservoir 312 of the extraction device 300 of FIG. 3. The solvent inlet 316 is functionally similar to the solvent inlet 116 of the embodiments shown in FIGS. 1A-1B. However, in the embodiment shown in FIG. 3, the solvent inlet 316 rises higher from the top surface of the solvent reservoir 312 to ensure that it rises above the level of the cold bath contained within the outer tank 314. Additionally, the solvent inlet 316 may function as a valve to release gas that may be trapped within the device 300.

The solvent reservoir 312 of the embodiment shown in FIG. 3 is constructed in a similar manner and geometry as the solvent reservoir 112 of the embodiment shown in FIGS. 1A-1B. As detailed above, the solvent reservoir 312 has thin walls that allow for rapid thermal energy transfer across their cross-section, the rapid flow of thermal energy ensuring that the solvent contained within the solvent reservoir 312 maintains a sufficiently low energy state such that the solvent is kept in a liquid phase.

A view port 319 is disposed on the solvent reservoir 312, extending through the outer tank 314 to the exterior of the device 300. The view port 319 is similar to the view port 118 of the device 100 of FIGS. 1A and 1B. The view port 319 is constructed of a transparent material set into a metal housing and can include lighting elements, such as LEDs, used to illuminate the interior of the solvent reservoir 312. A user can observe the interior of the solvent reservoir 312 through the view port 319 to assess the amount of solvent within the tank and monitor the solvent recovery process.

The outer tank 314 of the embodiment shown in FIG. 3 is constructed in a similar manner, geometry and materials as the outer tank 114 detailed in the embodiment shown in FIGS. 1A-1B. The sidewalls of the outer tank 314 are necessarily higher than the tank 114, in order to contain the cold bath around not only the solvent reservoir 312 but the condensing coil 315 as well.

The cold bath contained within the outer tank 314 should be of a sufficiently low temperature to recondense the returning gaseous solvent. The solvent used in the embodiment of FIG. 3 is butane, which has a boiling point of −1° C. The surrounding bath needs to be able to chill the gaseous solvent in solvent reservoir 312 and condensing coil 315 to a temperature at least below the solvent boiling point in order to recondense the solvent into a liquid phase. The dry ice and ethanol bath used in the embodiment of FIG. 3 has a temperature of approximately −78° C. This significant temperature difference from the boiling point assists in recondensing the majority of the gaseous solvent to a liquid solvent. Additionally, the large temperature variation between the solvent reservoir 312 and the collection reservoir 352 helps drive the recycling of the solvent from the collection reservoir 352 and back into the solvent reservoir 312.

Alternatively, a bath of dry ice pellets, ethanol and ethylene glycol may be used. This alternate bath has a similar temperature but the temperature may be controlled by varying the ratio of ethylene glycol and ethanol. The addition of the ethylene glycol raises the temperature of the bath but still maintains it at a level to recondense the gaseous solvent to its liquid state. The alternate bath also has the added benefit of maintaining its low temperature for a longer period of time. The ethylene glycol has a freezing point of −13° C., which is higher than that of the dry ice. The ethylene glycol and ethanol form a gel-like substance when mixed with the dry ice, this gel-like substance can maintain a lower bath temperature for a longer period of time than the ethanol and dry ice bath. The cold bath increases the temperature differential between the collection tank and the solvent tank, which improves the overall efficiency of the extraction process.

The solvent storage chamber 310 is connected to the extraction chamber 330 via a connector 320. The connector 220 has a valve 322 and a transparent section 324 disposed therein. The valve 322 functions similarly to the valve 122 of the embodiment detailed in FIGS. 1A-1B, controlling and regulating the flow of the solvent from the solvent reservoir 312 into the extraction chamber 330. The addition of the transparent section 324 to the connector 320 allows a user to view the flow of solvent from the solvent reservoir 312 through the connector 320. A user viewing the flow can determine if a greater or lesser flow rate is desirable and can adjust the valve 322, manually or electronically, as needed. The solvent storage chamber 310 and the extraction chamber 330 may be permanently or releasably connected to the connector 320. In the embodiment shown in FIG. 3, both chambers 310 and 330 are releasably connected to the connector 320 using a sanitary connection.

The extraction chamber 330, as shown in the embodiment detailed in FIG. 3, features the plant material chamber 332 having a top 334 and a bottom 336. The plant material chamber 332 is surrounded by an outer tank or jacket 333 that contains a warm or hot bath. The jacket 333 may be a second flexible or rigid tank that surrounds the plant material chamber 332 or both may be integrated into a single unit. As shown in the embodiment of FIG. 3, the plant material chamber 332 features a double-wall construction, similar to that found on insulated double-wall coolers. The inner walls of the chamber 332 house the plant material and the outer walls form the jacket 333. In this manner, the chamber 332 is attached and disposed in the center of the surrounding jacket 333.

A source of a warm/hot bath is connected to the jacket 333 through ports 335 and 337. The source of the warm/hot bath may be controlled to an exact temperature, a temperature range, or just generally warm/hot, depending on the temperature gradient that is desired. The warm/hot bath, typically heated water, flows from a source (not shown) through port 337, where it rises and surrounds the chamber 332 before exiting through port 335. In the embodiment shown, the chamber 332 is constructed from a material capable of rapid thermal energy transfer across the sidewalls of the chamber 332. The rapid thermal energy transfer allows the heat from the surrounding warm/hot bath to penetrate the chamber walls and warm the material and solvent/solvent-extract solution contained.

The plant material stored within the plant material chamber 332 is warmed to assist in recovery of the solvent trapped within the plant material after the extraction process has completed. By encircling the chamber 332 with the hot/warm jacket 333, the temperature of the material in the chamber 332 can be raised sufficiently high, after the extraction process, to volatilize remaining solvent. This gaseous solvent can then be recovered for later use and/or storage.

The plant material chamber 332, as shown in the embodiment of FIG. 3, has solid sidewalls. View ports 339a and 339b are disposed about the periphery of the plant material chamber 332 to allow the user to view and observe the interior of the plant material chamber 332. The view ports 339a and 339b extend from the chamber 332 through the surrounding bath and jacket 333. The view port 339a is located at an upper portion of the plant material chamber 332 and the view port 339b is located at a lower portion.

The view ports 339a and 339b allow the device 300 user to monitor and observe the majority of the interior of the plant material chamber 332. Additionally, as in the solvent reservoir 312, the plant material chamber may feature internal markings indicating the quantity of plant material, solvent and/or other material stored within the plant material chamber 332. Further, additional view ports may be installed on the plant material chamber 332 as necessary or as desired. The view ports 339a, 339b and/or additional view ports may feature integrated light sources, such as LEDs or other suitable lighting devices that illuminate the plant material chamber 332 interior. Alternatively, the plant material chamber 332 may be constructed of a thermally conductive transparent material that would allow a user to view the internal contents of the plant material chamber 332 through the surrounding hot/warm bath in the jacket 333.

The top 334 and/or bottom 336 of the plant material chamber 332 may be releasably or permanently affixed to the chamber 332. In the embodiment shown in FIG. 3, the top 334 and/or bottom 336 is releasably affixed to the plant material chamber 332 using a sanitary connection such as a hinged clamp. In the embodiment of FIG. 3, a user may access the interior of the plant material chamber 332 through the top 334 and/or the bottom 336, both of which are open ring-like structures. The extraction chamber 330 may be removed from the device 300, the top 334 or bottom 336 may then be removed from the chamber 332 to allow a user greater access to the interior of the chamber 332. Access to the chamber is required for the user to place the material containing the extractable compound(s) within it. The plant material chamber 332 with the top 334 and bottom 336 in place are sealed and house the material, solvent, and solvent-extract solution. Alternatively, instead of having a removable top 334 or bottom 336, a sealable access may be disposed on one or both surfaces. The access provides a way for a user to access the interior of the plant material chamber 332, such as by an access door, for example.

The plant material chamber 332 or the bottom 336 can include a filter that prevents solid material housed within the extraction chamber 332 from passing through the connector 340 and entering the collection reservoir 352. Alternatively, the filter may be disposed in an intervening structure between the extraction chamber 330 and the collection chamber 350. The filter could include a mesh screen, a paper filter or a semi-permeable membrane through with the solvent-extract solution may pass.

The extraction chamber 330 is connected to the collection chamber 350 via a connector 340. The extraction chamber 330 may be permanently or releasably connected to the connector 340. The connector 340 has a valve 342 and a transparent section 344 disposed therein. The valve 342 functions similarly to the valve 122 of the embodiments detailed in FIGS. 1A-1B, regulating and controlling the flow of the solvent-extract solution from the plant material chamber 332 into the collection chamber 350. The addition of the transparent section 344 to the connector 340 allows a user to view the flow of the solvent-extract solution from the plant material chamber 332 through the connector 340. A user viewing the flow can determine if a greater or lesser flow rate is desirable and can adjust the valve 342, manually or electronically, as needed. The extraction chamber 330 and the collection chamber 350 may be permanently or releasably connected to the connector 340. In the embodiment shown in FIG. 3, both chambers 330 and 350 are releasably connected to the connector 340 by a sanitary connection.

The collection chamber 350 of the embodiment shown in FIG. 3 has a collection reservoir 352, a hot/warm bath jacket 354 having ports 353 and 355, an access 357, the access having a view port, and a solvent return outlet 384.

As with the collection reservoir 152 of the embodiments shown in FIGS. 1A-1B, the collection reservoir 352 of the embodiment shown in FIG. 3 is constructed having similar geometry and material properties. As with the previous embodiment, the collection reservoir 352 is surrounded by a hot bath. In the embodiment shown in FIG. 3, the collection reservoir 352 is surrounded by a jacket 354, which contains the hot bath around the reservoir 352. The jacket 354 and the reservoir 352 are a single unit, constructed as a double-wall vessel, similar in manner to that found in insulated double-wall coolers. The inner walls of the unit form the reservoir 352 and the outer walls form the jacket 354. The space between the walls houses the hot/warm bath. The jacket 354 features ports 353 and 355, through which the hot/warm bath is introduced, discharged and/or recirculated. The ports 353 and 355 are connected to a hot/warm bath source that heats a medium. In this embodiment, the medium is water that is then pumped or fed through one of the ports.

The heated medium fills the space between the jacket 354 and the collection reservoir 352. The heated medium may be sealed in the jacket 354 until the extraction is done, then drained through a port. Alternatively, the heated medium can be continuously introduced through a port and discharged continuously through the other port, ensuring that a fresh supply of heated medium surrounds the collection reservoir 352 and ensuring the collection reservoir 352 and the solvent-extract solution stored within is kept at an ideal temperature or range of temperatures. The source of the hot/warm bath may be connected to the discharge port such that the hot/warm bath is constantly recirculating through the jacket 354, returning to the source to be reheated and recirculated. This is the method used in the embodiment as shown in FIG. 3, which may include an internal heater disposed within the jacket 354 that further heats or maintains the temperature of the surrounding hot/warm bath, as necessary.

In another embodiment, the heated medium may be pumped into the jacket 354 and left there, a separate heater disposed within the jacket maintaining the desired temperature of the medium. In another embodiment, the jacket 354 may be filled with a medium that may be heated by an internal or external source. The jacket can be filled with the heated medium prior to or during an extraction cycle. Once the extraction cycle(s) is completed, the medium is allowed to cool and is then reheated during the next extraction cycle(s). The medium may be sealed within the jacket 354 permanently and heated as necessary, or may be replaceable or replenished as needed through port(s) disposed on the jacket that allow for changing the medium or adding additional medium.

In the embodiment shown in FIG. 3, the connector 340 extends through the top surface of the collection reservoir 352. The connector 340 extends into the interior of the collection reservoir 352, with the end of the connector 340 located at a point below the outlet 384. The extension of the connector 340 helps to prevent solvent-extract solution from being drawn through the outlet 384 and helps prevent solvent vapor from traveling into the plant material chamber 332. Since the system is sealed, as the solvent is dispensed from the solvent reservoir 312, the return 380 can act as a siphon if the valve 382 is open. The siphon effect could potentially draw the solvent-extract solution through the outlet 384 and up the return 380. Also, the solvent vapor is light-weight and has a tendency to rise to the top of the reservoir 352. By terminating the connector 340 below the outlet 384, solvent vapor is less likely to travel back through the connector 340. This is especially true when the level of the solvent-extract solution is above the termination point of the connector 340. This forms a liquid barrier to the solvent vapors traveling back through the connector 340 and up the various sections and connections of the device 300.

The access 357 of the embodiment shown in FIG. 3 allows a user to access the contents of the collection reservoir 352. The access 357 is sealed by a cap that prevents contaminants from entering the solvent-extract or extract solution stored within the collection reservoir 352. Other suitable releasable options for sealing the access 357 exist and may be used. The cap sealing the access 357 may also feature a view port to allow the user to observe and/or monitor the contents and activity within the reservoir 352. Further, this view port may feature the lighting feature as discussed above to further enhance a user's view into the reservoir. Additionally, the interior of the collection reservoir 352 may feature markings or indications to indicate the fill level or other features of the solution or materials within the collection reservoir 352.

A pressure indicator, such as the pressure gauge 170 of the embodiment shown in FIGS. 1A-1B, may be disposed on the collection chamber 350 although it is not shown in FIG. 3. The indicator may be disposed on the upper surface of the reservoir 352 or on the cap that seals the access 357. Alternatively, the indicator may be disposed on the jacket 354 may be in fluid communication with the collection reservoir 352 in order to sense and display the internal pressure of the device 300. Further embodiments include an electronic pressure sensor that transmits and indicates a pressure on a display located externally of the device.

The solvent return 380 is a path for the solvent vapors to travel from the reservoir 352 to the condensing coil 315. As the solvent extract solution is heated in the reservoir tank 352, the solvent volatilizes into a gaseous phase. In the gaseous phase, the solvent can flow through the outlet 384, through the return 380 and into the condensing coil 315 through the inlet 386. The return 380 has a valve 382 and a transparent section 383 disposed therein. The valve 382 regulates the flow of solvent vapors through the return 380. The valve 382 may be controlled manually or electronically by a user or a controller. The transparent section 383 allows a user to observe the flow of the solvent vapors through the return 380, which may be desirable or necessary in order to determine the regulation of the vapor through the valve 382.

The solvent return may also include an oxygen purge element. In the embodiment shown in FIG. 3, the purge is a valve 388 disposed on the return 380. The valve 388 allows the user to purge or decrease the amount of oxygen within the device 300 before starting an extraction process and/or loading the solvent. When using a combustible or flammable solvent, the purging of oxygen from the system assists in lowering the risk of solvent ignition. The valve 388 may be a one-way valve or may be actuated by a user or other control means. The purge of oxygen or other atmosphere within the device may be accomplished by introducing a secondary, inert gas that displaces the existing gas within the device 300 through the valve 388. Alternatively, a vacuum can be created within the device, the evacuated air being drawn through the valve 388 by a mechanical means. By creating a vacuum or low pressure within the device, the amount of oxygen within the device is preferably below the level required for ignition and/or combustion of the solvent.

Additionally, the return 380 as shown in the embodiment of FIG. 3 also includes a support 387 that contacts the base/ground 360. The support 387 is a stand that stabilizes the return 380. The return 380 may be connected to sections of the device to provide additional stability and structure to the device as necessary. In the embodiment shown in FIG. 3, the return 380 is connected to the solvent storage chamber 310 to assist with stabilizing that section. The return 380 of this embodiment is therefore made of a structural material such as metallic pipe or other suitable material that can withstand the forces required to provide support to the device 300.

The embodiment of the device 300 of FIG. 3 may be scaled larger or smaller as necessary depending on the size of the extraction batches a user intends to run. All the sections can be made requisitely smaller or larger depending on the anticipated user needs. The materials used for constructing the device 300 should be at least non-reactive with the solvent, plant material and the extracted compounds. Preferably, the materials used are of food and/or medical grade quality, but other suitable materials can be used. Additionally, sanitary connections are preferably used throughout the device 300 for all releasable connections. However, other suitable releasable connections can be used, such as threaded connections.

The chambers 310, 330 and 350, the connectors 320 and 340 and the return 380 of the device 300 of FIG. 3 are releasably connected using various releasable fittings and connection means. This allows the various sections to be removed, stored, serviced, replaced, sold separately, maintained and cleaned individually as necessary.

A pump may be used to extract, move and recompress the gaseous solvent from the collection reservoir 352 into the solvent reservoir 312. The pump would need to be suitable for moving the gaseous solvent, i.e., fire rated to minimize the potential for explosions and food safe so as to not contaminate the recovered solvent. For example, the extraction systems can include a hydrocarbon-rated pump that does not exceed 100 psi and can be placed in-line with the return and/or could access any of the device chamber(s) to aid in the extraction process. The pump could be added to the disclosed system or could replace the return 380 and minimize or eliminate the need for the baths and the condensing coil 315.

The pump creates low pressure in the collection reservoir causing the solvent to boil off from the solvent-extract solution due to the low vapor pressure within the collection reservoir 352. The gaseous solvent would then be pumped into the solvent reservoir 312 under pressure. The increased pressure would cause the gaseous solvent to recondense into a liquid phase. Alternatively, the cold bath about the solvent reservoir 312 could be used to assist in the recondensing of the gaseous solvent, lessening the pressure required from the pump. A hot/warm bath may also be utilized to assist with the separation of the solvent from the solvent-extract solution.

Figure 4:
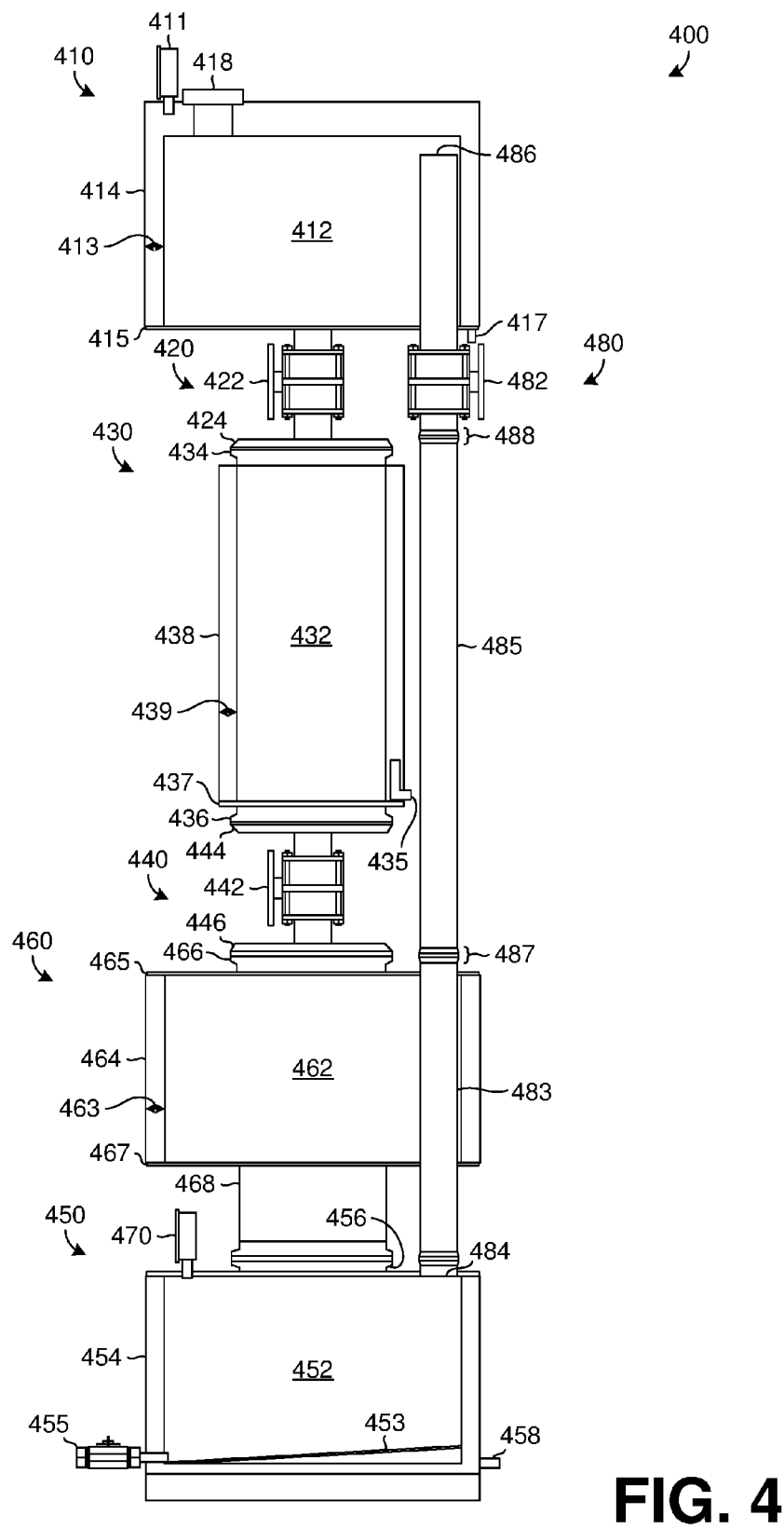
FIG. 4 is yet another example extraction device according to aspects of the disclosure.

FIG. 4 is a further embodiment of an extraction device 400, the device 400 including a refinement chamber 460 disposed between the extraction chamber 430 and the collection chamber 450.

The device 400 includes a solvent chamber 410, a connector 420, an extraction chamber 430, a connector 440, a refinement chamber 460, a collection chamber 450 and a solvent return 480. The device 400 of FIG. 4 is substantially the device 200 of FIG. 2A with the addition of the refinement chamber 460.

A solvent chamber 410 includes a solvent reservoir 412, an outer wall 414 spaced a distance 413 from the reservoir 412, a shared base 415 and a view port 418. Optionally, the solvent chamber can include a pressure gauge 411 and a solvent inlet (not shown). The pressure gauge 411 can indicate a positive pressure, a negative pressure or a combination thereof.

The solvent reservoir 412 contains the liquid solvent and is surrounded by an outer wall 414 spaced a gap 413 away. The gap 413 can be filled with a temperature bath to heat or preferably cool the solvent reservoir 412 to assist with the recovery of the solvent used during the extraction process. A drain 417 is included on the shared base 415 to assist with draining the temperature bath from between the outer wall 414 and the solvent reservoir 412.

The solvent reservoir is connected to and in fluid communication with the connector 420. The connector 420 includes a sanitary valve 422 and a sanitary cap 424. As in the device 200 of FIG. 2A, a solvent return 228 can be affixed to the sanitary cap 424. The solvent return allowing fluid communication between the solvent reservoir 412 and the plant material chamber 432.

The extraction chamber 430 includes a plant material chamber 432, surrounded by an outer wall 438 set a distance 439 from the chamber 432 and a shared base 437. The plant material chamber 432 includes an affixed or integrated top sanitary ferrule 434. The sanitary ferrule 434 interfaces with the sanitary cap 424 to form a sanitary connection when the chamfered circumferences of each are compressed using a clamp such as a single pin-hinged clamp.

The gap 439 between the outer wall 438 and the plant material chamber 432 can be filled with a temperature bath. Preferably the gap 439 is filled with a hot or warm water bath after the extraction is complete. The heating of the solvent-ladened plant material within the plant material chamber 432 volatilizes the entrapped solvent so that it may be recovered for later extraction processes. A drain outlet 435 is included to drain the temperature bath from the gap 439.

A bottom sanitary ferrule 436 is affixed or integrated to the shared base 437. The bottom sanitary ferrule 436 can include a filter designed to exclude or prevent plant material from the plant material chamber 432 from traveling through the remainder of the device 400.

A connector 440 connects and facilitates fluid communication between the extraction chamber 430 and the refinement chamber 460. The connector 440 includes a sanitary valve 442, a top sanitary cap 444 and a bottom sanitary cap 446. The top sanitary cap 444 interfaces with the bottom sanitary ferrule 436 to form a sanitary connection that can be clamped together about the periphery of the chamfered circumferences of the pieces 444 and 436.

The bottom sanitary cap 446 of the connector 440 interfaces with the top sanitary ferrule 466 of the refinement chamber 460. As discussed above, the interfacing of the sanitary cap 440 and sanitary ferrule 446 forms a sanitary connection linking the connector 440 and the refinement chamber 460.

The refinement chamber 460 includes a refinement reservoir 462, an outer wall 464 spaced a distance 463 about the reservoir 462, a top 465 and a base 467, and bottom sanitary ferrule 468.

The gap 463 is preferably filled with a cold temperature bath. The extract-rich solvent solution is transferred from the extraction chamber 430 through the connector 440 and into the refinement chamber 460. The cold refinement chamber solidifies impurities such as waxes that were extracted from the plant material, the solidified impurities can then be filtered from the extract. The cold temperature can also thicken the heavier or denser extracted oils, which may not be desirable in the final product. These thickened oils can also be filtered from the extract solution. Additionally, the extract-rich solvent solution can sit in residence for a set amount of time within the refinement reservoir 462. The residence time within the reservoir 462 can allow impurities to settle out from the solution, the refined solution can then be transferred into the collection chamber 450.

A filter can be placed within the bottom sanitary ferrule 468. The filter can be designed to remove solids, such as waxes, and/or filter heavier oil components from the extract-rich solvent solution. The waxes and/or oils can be recovered from the filter and used in other commercial products or processes.

Once the extract-rich solvent solution is sufficiently refined in the refinement chamber 460, the solution is transferred into the collection chamber 450 through the sanitary ferrule 456 disposed atop the collection reservoir 452.

The collection chamber 450 includes a collection reservoir 452, an outer tank 454 and an extract outlet 455. A hot or warm temperature bath is constrained about the collection reservoir 452 by the outer tank 454, heating the extract-rich solvent solution within the reservoir 452. The solvent is volatilized and travels through the solvent return 480 into the solvent reservoir 412 where it recondensed into liquid solvent that can be used for other extractions.

An inclined floor 453 can be included in the collection reservoir 452 to assist with the collection of the extract through the outlet 455. The inclined floor 453 can be placed in or integrated with the collection reservoir 452. Alternatively, the collection reservoir 452 can be constructed with a sloped base.

A drain outlet 458 is disposed on the outer tank 454 to assist with draining the enclosed temperature bath.

A pressure indicator 470, similar to the pressure indicator 170 of FIGS. 1A and 1B, is in fluid communication with the interior of the collection reservoir 452. The pressure indicator 470 allows a user to observe and monitor the interior pressure of the collection reservoir 452.

The solvent return 480 is connected to the collection reservoir 452 at an inlet 484. In the embodiment shown in FIG. 4, the solvent return 480 is substantially the same as the solvent return 280 of FIG. 2A. The solvent return 480 includes a conduit extension piece 483 that is inserted in the return 480, lengthening the return 480 to account for the addition of the refinement chamber 460. The conduit extension piece 483 is connected to the main conduit 485 using a sanitary connection 487.

The various connections, 487 and 488, along the length of the solvent return 480 are accomplished using suitable sanitary connections. The use of sanitary connections throughout the device 400 assists in ensuring the purity of the extract.

The solvent return 480 includes a sanitary valve 482 that is used to control and regulate the flow of the volatilized solvent through the return 480.

The solvent return includes an outlet 486 that terminates in the solvent reservoir 412. The outlet 486 is positioned above the level of the liquid solvent within the reservoir 412. As the volatilized solvent exits the outlet 486, it is recondensed into liquid solvent. The elevated position of the outlet assists in preventing liquid solvent from flowing back down the return 480.

Extraction Process

The devices 100 and 200, disclosed above, are designed to perform closed-system plant extraction process and are discussed now using the device shown in FIG. 1 as an example. Plant material is placed in the device, which is then sealed. The extraction and recovery processes are then run, resulting in end products of recovered solvent and extracted plant compounds.

Prior to operating the device 100 or adding solvent to the solvent reservoir 112, any oxygen within the device 100 should be minimized or removed. This can be done by pulling a vacuum within the device through an external port such as valve 188. A user can check the pressure gauge 170 to observe when the device 100 has been evacuated. The devices can also include a vacuum gauge, not shown, in some examples to measure the vacuum level within the device. Alternative oxygen removal options can be used, such as the use of oxygen scavenging chemicals or sacrificial oxygen removal elements disposed within the device 100.

The solvent is disposed within the solvent reservoir 112, where it is maintained in a liquid phase due to the vapor pressure created by the solvent. Alternatively, the reservoir 112 may be chilled to assist in keeping the solvent in a liquid phase. Solvent is then released from the solvent reservoir 112 by the valve 120, the solvent then flows into the extraction chamber 132.

In the extraction chamber 132, the solvent contacts the material having extractable compound(s). The solvent flows over the material picking up and washing away the extractable compound(s), the solvent and extractables forming a solvent-extract solution. The residence time of the solvent on the material may be adjusted by varying the entry and exit flow rates of the valves 120 and 140 leading into and out of the extraction chamber 132.

The solvent-extract solution enters the collection reservoir 152 through the valve 140. Once the extraction is completed, the collection reservoir 152 is surrounded by a hot bath that heats the solvent-extract solution within the reservoir. It is desirable that the temperature of the bath is high enough to volatilize the solvent relatively easily, but low enough so as to not affect the extract(s).

Alternatively, during the extraction process, the collection reservoir 152 can be heated and the solvent reservoir 112 cooled. The solvent is dispensed from the solvent reservoir 112 and flows through the plant material in the plant material chamber 132. The solvent-extract solution then flows into the collection reservoir 152 where the solvent volatilizes. The gaseous solvent travels through the solvent return 180 and recondenses in the solvent reservoir 112. From there, the solvent may be recirculated through the extraction device 100 repeatedly. This alternative process performs a continuous recirculating extraction loop across the contained material.

As the solvent is heated by the hot bath, it undergoes a phase change from a liquid to a gas. In the gaseous phase, the solvent can flow through the outlet 184, up the solvent return 180, into the inlet 186 and finally recondenses in the cold solvent reservoir 112. The recycling of the solvent conserves the solvent for repeated cycles during the extraction process or for later use. By relying on the phase change properties of the solvent, no pumps or other mechanisms are required to move solvent through the device although a food-safe pump could be included as discussed above. As discussed above, a pump, rated for the solvent used and made of food safe materials, could be added to the device 100 to assist with and/or move the solvent from the collection reservoir 152 to the solvent reservoir 112.

Since the solvent is driven off of the solvent-extract solution due to heating of the solution within the collection reservoir 152, the remaining extract is left partially or completely purified. Once the extraction process is completed and all of the solvent-extract solution has collected in the collection reservoir 152, the hot bath is maintained to further volatilize the solvent. The solvent vapors are drawn up the solvent return 180, leaving behind purified product in the collection reservoir 152. The product may need further refining which can be performed by various means.

Extraction of Canabinoids

The device may be used to extract cannabinoids from marijuana plant material to form an oil or extract solution rich in cannabinoids, for example. The extraction process described below uses the device embodiment as shown in FIG. 2, however, it is understood that the process can be performed using other embodiments of the device as described herein. Other plant materials can be used with the disclosed extraction devices as well.

A user first removes or minimizes any oxygen within the device 200 or solvent reservoir 212 by evacuating the device 200 or solvent reservoir 212. The device 200 or solvent reservoir 212 can be evacuated by a vacuum or venturi pump that is connected to an external valve of the device, such as valves 285 or 287. Oxygen and other gases should be removed from the device 200 or solvent reservoir 212 for safety and efficiency. The removal of the oxygen will reduce the likelihood of combustion or explosion of the butane as the device 200 or solvent reservoir 212 is filled. Remaining oxygen and other gasses will also displace the butane as it is introduced to the device, which can cause the device 200 or solvent reservoir 212 to fill improperly or inefficiently.

The user then adds solvent to the solvent reservoir 212 of the solvent chamber 210. For the process described here, the solvent used is butane, preferably a food-grade, refined version of n-butane or isobutane.

To load the plant material into the plant material chamber 232, the user unclamps the sanitary connections between the sanitary cap 224 and top sanitary ferrule 234 and the bottom sanitary ferrule 236 and sanitary cap 244. The extraction chamber 230 can then be removed from the device 200. With the inner cavity of the plant material chamber 232 exposed, the user begins loading the material inside. The use of an extraction process allows cannabinoids to be obtained from parts of the plant often discarded such as the leaves and stems as well as the traditional buds. The plant material is packed into the plant material chamber 232 and the extraction chamber 230 is remounted into the device 200. The extraction chamber 230 is secured within the device 200 by clamping the sanitary cap 224 and top sanitary ferrule 234 and clamping the bottom sanitary ferrule 236 and sanitary cap 244. When clamping the bottom sanitary ferrule 236 and sanitary cap 244, the filter gasket can be inserted either between the two or within the plant material chamber 232.

Once the extraction chamber 230 is replaced within the device 200, the device 200 will need to be evacuated to remove oxygen. If the device 200 was previously evacuated before adding the solvent, the removal of the extraction chamber 230 will have exposed the interior of the device 200 to oxygen once again. The device 200 can be evacuated through one of the external valves, such as valve 285 or 287, by connecting a vacuum pump, venturi pump, or other suitable evacuation device. Once the device 200 has been suitably evacuated, this can be confirmed by the pressure indicator 270, the extraction process can begin.

To initiate the extraction process, the valve 220 is opened to allow the butane to flow from the solvent reservoir 212 and into the plant material chamber 232. Once the butane has flowed from the solvent reservoir 212 and into the plant material chamber 232, the valve 222 is left open to account for liquid expansion of the butane solvent. The butane then sits on the plant material extracting the cannabinoids. After a set amount of time or once the user observes the extraction process is complete through a view port, the solvent-extract solution is released from the plant material chamber 232 through the valve 240 and into the collection reservoir 252.

Once the extraction process has been completed and most of the solvent-extract solution has drained into the collection reservoir 252, the valve 222 is closed and a hot/warm bath is applied to the plant material chamber 232 using the jacket 233. A bath source is connected to the inlet 237 and the outlet 235. The source could be simply a hot water tap or a water heating and recirculation unit. If using a hot water tap, the tap is connected via a line to the inlet 237 and the outlet is connected to a line that runs to a drain. If using a heating/recirculating unit, the inlet and outlet are run to the unit so that the hot/warm bath may be continuously heated and distributed through the jacket 233. The hot/warm bath about the plant material chamber 232 volatilizes remaining solvent so that it may be recovered through the collection reservoir 252.

The hot/warm bath source is connected to jacket 254 of the collection chamber 250. The source of the bath may be the same or different than the source of the bath used in the extraction chamber. It may be desirable for the bath surrounding the collection chamber 250 to be a higher temperature than the temperature of the bath surrounding the extraction section in order to volatilize the butane faster and/or more efficiently.

Alternatively, the baths of the extraction chamber 230 and the collection chamber 250 may share the same source, a heating/recirculating unit, the source heating water to a temperature desired for the collection chamber 250. The bath has an initial temperature when it enters the jacket 254 of the collection chamber 250 through the inlet 258a. The water then fills and surrounds the reservoir 252, imparting thermal energy to the reservoir 252 and the chamber 250. The water finally exits the port 258b at a second temperature. The upper jacket outlet 258b of the collection chamber 250 is connected to the jacket inlet 233a of the extraction chamber 230. The bath could flow from the jacket of the collection chamber 250 into the jacket of the extraction chamber 230 at the second temperature. The bath then circulates through the gap 239 of the extraction chamber 230, imparting thermal energy to the extraction chamber 230, the plant material chamber 232 and the enclosed plant material, before exiting through port 233b. After exiting port 233b, the bath can be returned to a heating/recirculation unit, where the water is reheated and again pumped through the jackets 254 and gap 239. Alternatively, the bath can be discarded after exiting port 233b, with new, heated bath fluid introduced through the inlet 258a.

Once a user has observed or believes the majority of the trapped solvent in the plant material chamber has been volatilized and has flowed into the collection reservoir 252, the valve 222 is closed. The solvent-extract solution, now in the collection reservoir 252, is warmed by the surrounding hot/warm bath contained in the jacket 254. As the solution heats, the butane boils and undergoes a phase change into a gaseous state. The butane gas then flows to the outlet sanitary ferrule 284 and into the solvent return 280, through which it rises. The gas exits the solvent return 280 through the outlet 286, directly into the solvent reservoir 212, to be recovered. Alternatively, the solvent can return through a condensing coil 315, as shown in FIG. 3, to be cooled for recovery. As the gas flows through the coil, the surrounding cold bath, contained by the outer tank 214, causes the butane gas to condense back into a liquid phase. The mostly liquid butane re-enters the solvent reservoir 212, where it can then be held for later extraction use or fed back through the device 200.

The extraction process using the device 200 may be a circulatory process in which the butane flows through the cascaded sections as a liquid and returns to the top as a gas where it recondenses back into a liquid. Such a process conserves the butane solvent and allows for the recovery of it for use in later extractions or for other purposes.

As the hot/warm bath is being applied to the solvent-extract solution in the reservoir 252, the user is chilling the solvent reservoir 212 and condensing coil 315. The solvent reservoir 212 and condensing coil 315 are chilled by a surrounding cold bath composed of liquid alcohol and dry ice pellets. This cooling of the solvent reservoir 212 and condensing coil 315 assists in drawing the gaseous solvent through the solvent return 280 so that it may be condensed and stored within the solvent reservoir 212.

The extract remaining in the collection reservoir 252 is rich in cannabinoid extracts and may be further refined externally or internally of the device as necessary or desired. External refinement may include placing the solution under a vacuum to further remove any remaining butane. Other refinement techniques exist and are known and may be used to refine the extracted material.

Other plant material may be used to extract other desired compounds, such as but not limited to, essential oils.

Additionally, to perform the extraction, other solvents may be used, such as other hydrocarbons, refrigerants such as R-134a, and alcohols, as long as they are in ratios that do not exceed the operational pressure specifications of the device as set forth by the manufacturer. The selected solvent should extract the desired compounds from the material and have a boiling point below that of the extracted material so that the solvent may be separated by heating the resulting solvent-extract solution. The properties of the selected solvent determine the temperature gradient required to cycle the solvent through the device. The temperature gradient sets the temperatures of the cool and hot/warm baths.

Purification of Butane

The device may also be used to refine butane to a higher purity without the plant material present. The butane is disposed in the device as in the other examples, in the solvent storage tank 212. The butane is then dispersed through the plant material chamber 230 and into the collection reservoir 252 even though no plant material extraction occurs during the butane purification process. Alternatively, a direct connection between the solvent storage chamber 210 and the collection chamber 250 may be used in this case, thus bypassing the need to insert the extraction chamber 230 into the device 200. Once the butane has collected in the collection reservoir 252, it is heated and volatilized by the surrounding hot/warm bath. Simultaneously, the user chills the solvent storage chamber 210 using a cold bath. The now gaseous butane flows from the collection reservoir 252, through the return 280 and into the solvent storage section 210. As the gaseous solvent contacts the now-chilled solvent storage chamber 210, it begins to condense in the coil 215. The resulting purified liquid solvent is then captured in the solvent storage tank 212.

Butane, as with many substances, has a specific boiling point. In the case of butane, the boiling point is a range of –2° C. Having such a narrow boiling point, it is possible, through careful temperature control of the bath surrounding the collection reservoir 252, to hold the butane at the critical boiling temperature, thus ensuring that the emanating gaseous vapors are predominately gaseous butane. By circulating the butane through the device repeatedly, the butane refines and becomes purer. The remaining materials left in the collection reservoir 252 after the purification has completed are miscellaneous hydrocarbons and other pollutants that were left in the butane during the manufacturing process. The user is left with high-purity liquid butane in the inner tank 212. This purified butane can then be used to run extraction processes or can be sold commercially.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing the invention in diverse forms thereof.

The invention claimed is:

1. An extraction method, comprising:
   causing, via a controllable solvent reservoir flow control feature, at least a portion of a stored solvent in a liquid phase that is stored in a solvent reservoir to be released through a first connector and into a plant material reservoir structured to be in fluid communication with the solvent reservoir;
   exposing plant material housed in the plant material reservoir to the released solvent in the liquid phase to produce a solvent-extract solution;
   releasing at least a portion of the solvent-extract solution from the plant material reservoir into a collection reservoir;
   causing at least a portion of the solvent to separate from the solvent-extract solution in the collection reservoir to produce an a solvent in a gaseous phase and extracts;
   releasing at least a portion of solvent the solvent in a gaseous phase from the collection reservoir into a solvent return, the solvent return providing fluid communication between the collection reservoir and the solvent reservoir;
   manipulating a controllable solvent return flow control feature to selectively cause at least a portion of the solvent in a gaseous phase to flow through the controllable solvent return flow control feature;
   and in one or both of the solvent return and the solvent reservoir, causing a solvent in the gaseous phase to re-condense from the gaseous phase back into the liquid phase;
   recovering the solvent in the liquid phase in the solvent reservoir, the solvent return forming a sealed, closed-cycle solvent recovery pathway between the collection reservoir and the solvent reservoir.

2. The extraction method of claim 1, further comprising causing one or both of the stored solvent in the solvent reservoir and the solvent in the liquid phase released into the plant material reservoir to be cooled to a cooling temperature below a temperature of the solvent-extract solution in the collection reservoir to create a temperature gradient between the solvent reservoir and the collection reservoir, and further comprising, adjusting the cooling temperature in one or more of the solvent reservoir, the solvent return, and the collection reservoir to control the temperature gradient.

3. The extraction method of claim 1, further comprising causing the solvent in a gaseous phase into the solvent reservoir from the solvent return to be cooled, the solvent in a gaseous phase cooled to a temperature below a boiling point of the solvent, which causes the solvent in the gaseous phase to re-condense from the gaseous phase back into the liquid phase.

4. The extraction method of claim 1, further comprising cooling the solvent reservoir with a cold source stored in a solvent reservoir housing that surrounds the solvent reservoir.

5. The extraction method of claim 1, further comprising causing the stored solvent in the liquid phase in the solvent reservoir, the plant material, the solvent-extract solution, and the solvent in the gaseous phase to be one or the other of cooled or exposed to heat to assist with one or both of producing the solvent-extract solution and recovering the solvent in the gaseous phase in the solvent reservoir.

6. The extraction method of claim 1, further comprising controlling at least one of a controllable solvent reservoir flow control feature and the controllable solvent return flow control feature with an electronic controller.

7. The extraction method of claim 1, further comprising causing the solvent-extract solution to be received in a refinement reservoir before the solvent-extract solution is released into the collection reservoir, and further comprising causing the solvent-extract solution to be exposed to a refinement solvent in the refinement reservoir to produce a refined solvent-extract solution, and further comprising causing the refined solvent-extract solution to be released, via a controllable refinement reservoir valve, through a third connector into the collection reservoir.

8. The extraction method of claim 1, further comprising causing at least one or more of a gas or a fluid to be released from the sealed, closed-cycle solvent recovery pathway by a purge valve.

9. The extraction method of claim 1, further comprising releasing the portion of the solvent in the gaseous phase from the collection reservoir directly into the solvent return.

10. The extraction method of claim 1, further comprising preventing flow between the plant material reservoir and the collection reservoir of one or more compounds from at least one of the plant material, the solvent, the solvent-extract solution by using a filter positioned inline with a second connector disposed between the plant material reservoir and the collection reservoir.

11. The extraction method of claim 1, further comprising releasing at least one of a selectively releasable connector positioned inline between one or more of the solvent reservoir, the plant material reservoir, the collection reservoir, and the solvent return and securing, by the at least one of the selectively releasable connector, the one or more of the solvent reservoir, the plant material reservoir, the collection reservoir, and the solvent return to another one of the solvent reservoir, the plant material reservoir, the collection reservoir, and the solvent return.

12. The extraction method of claim 1, wherein the manipulating the controllable solvent return flow control feature to selectively cause at least a portion of the solvent in the gaseous phase into the solvent return includes manipulating the controllable solvent return flow control feature to release at least a portion of the solvent in the gaseous phase into the solvent return positioned external to the plant material reservoir and the collection reservoir.

13. The extraction method of claim 1, wherein the manipulating the controllable solvent return flow control feature to release at least a portion of the solvent in the gaseous phase into the solvent return includes manipulating the controllable solvent return valve to release at least a portion of the solvent in the gaseous phase into the solvent return that is at least partially positioned internal to the plant material reservoir and the collection reservoir.

14. The extraction method of claim 1, wherein the at least a portion of the solvent-extract solution is released from the plant material reservoir directly into the collection reservoir.

15. The extraction method of claim 1, further comprising activating a pump disposed in fluid communication with the solvent return, the pump configured to alter pressure in one of more of the solvent chamber, the plant material chamber, the collection chamber, and the solvent return.

16. An extraction method, comprising:
storing solvent in a liquid phase in a solvent chamber having a solvent chamber port;
selectively releasing, via a controllable solvent chamber fluid flow control feature, the solvent in the liquid phase into an extraction pathway from the solvent chamber into a plant material chamber through a solvent chamber-plant material chamber connector positioned between the solvent chamber and the plant material chamber and structured to be in fluid communication with the solvent chamber;
housing plant material in the plant material chamber;
exposing the plant material housed in the plant material chamber to the released solvent in the liquid phase received in the plant material chamber to produce a solvent-extract solution;
releasing at least a portion of the solvent-extract solution from the plant material chamber into a collection chamber structured to be in fluid communication with the plant material chamber along the extraction pathway;
causing at least a portion of the solvent-extract solution in the collection chamber to separate into solvent in a gaseous phase and extract;
releasing, along a recovery pathway, at least a portion of the solvent in the gaseous phase into a solvent return that is structured to provide fluid communication for the solvent in the gaseous phase to travel along the recovery pathway towards the solvent chamber, the releasing of the solvent in the gaseous phase controlled by a fluid flow control feature positioned to selectively regulate flow of the solvent in the gaseous phase through the solvent return;
causing the at least a portion of the solvent in the gaseous phase released into the solvent return to re-condense into the solvent in the liquid phase; and
recovering the solvent in the liquid phase in the solvent chamber.

17. The extraction method of claim 16, further comprising selectively releasing at least one of a fluid or a gas from the solvent return by actuating a purge valve when a predetermined threshold pressure is reached within one or both of the collection chamber and the solvent return.

18. The extraction method of claim 17, wherein the selectively releasing at least one of a fluid or a gas from the solvent return includes automatically actuating the purge valve when the predetermined threshold pressure is reached within one or both of the collection chamber and the solvent return.

19. The extraction method of claim 16, wherein the causing the at least a portion of the solvent in the gaseous second phase released into the solvent return to re-condense into the solvent in the first liquid phase includes one or both of (i) exposing the solvent-extract solution to heat and (ii) cooling one or both of the solvent chamber and the solvent return.

20. The extraction method of claim 16, wherein the causing the solvent in the gaseous phase released into the solvent return to transform into the liquid phase includes creating a temperature gradient between the solvent in the gaseous phase and the solvent chamber in which the solvent in the gaseous phase is caused to re-condense to the liquid phase based on one or both of a higher pressure of the solvent in the gaseous phase and a pump, one or both of which cause the solvent in the gaseous phase to travel along the extraction pathway to be recovered in the solvent chamber.

21. The extraction method of claim 16, wherein the releasing of the at least a portion of the solvent in the gaseous phase into the solvent return includes releasing the at least a portion of the solvent in the gaseous phase directly from the collection chamber into the solvent return to be recovered into the solvent chamber.

22. The extraction method of claim 16, wherein the releasing of the solvent in the gaseous phase into the solvent return includes releasing the solvent in the gaseous phase back into the plant material chamber and then releasing the solvent in the gaseous phase from the plant material chamber into the solvent return.

23. The extraction method of claim 22, wherein the releasing of the solvent in the second phase back into the plant material chamber and then into the solvent return includes causing the solvent in the gaseous phase to directly exit from the plant material chamber into the solvent return for recovery into the solvent chamber.

24. The extraction method of claim 16, further comprising activating a pump disposed in fluid communication with the solvent return, the pump configured to alter pressure in one of more of the solvent chamber, the plant material chamber, the collection chamber, and the solvent return.

25. The extraction method of claim 16, wherein the releasing of the at least a portion of the solvent-extract solution from the plant material chamber includes controlling the release of the at least a portion of the solvent-extract solution by a plant material chamber fluid flow control feature and causing the released at least a portion of the solvent-extract solution to travel through a plant material chamber-collection chamber connector positioned between the plant material chamber and the collection chamber.

26. The extraction method of claim 16, further comprising releasing one or more selectively releasable connectors positioned inline along the extraction pathway between two or more of the solvent chamber, the plant material chamber, the collection chamber, and the solvent return.

27. The extraction method of claim 16, further comprising preventing flow along the extraction pathway of one or more compounds of the solvent, the plant material or the solvent-extract solution by using at least one of a filter positioned inline the extraction pathway between or within one or more of the solvent chamber, the plant material chamber, the collection chamber, and the solvent return.

28. The extraction method of claim 16, wherein the releasing the at least a portion of the solvent in the gaseous phase includes actuating the fluid flow control feature with an electronic controller.

29. The extraction method of claim 28, wherein the electronic controller is programmed to actuate the fluid flow control feature based on one or more of a pressure within the collection chamber, a pressure within the plant material chamber, a pressure within the solvent return, a temperature within the collection chamber, a temperature within the plant material chamber, a temperature within the solvent chamber, and a temperature within the solvent return.

* * * * *